(12) United States Patent
Platt et al.

(10) Patent No.: US 8,153,592 B2
(45) Date of Patent: Apr. 10, 2012

(54) MODULATING TOLL-LIKE RECEPTOR ACTIVITY

(75) Inventors: Jeffrey L. Platt, Rochester, MN (US); Gregory J. Brunn, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 182 days.

(21) Appl. No.: 11/813,652

(22) PCT Filed: Jan. 10, 2006

(86) PCT No.: PCT/US2006/000864
§ 371 (c)(1),
(2), (4) Date: Jul. 10, 2007

(87) PCT Pub. No.: WO2006/074464
PCT Pub. Date: Jul. 13, 2006

(65) Prior Publication Data
US 2009/0111746 A1 Apr. 30, 2009

Related U.S. Application Data

(60) Provisional application No. 60/642,872, filed on Jan. 10, 2005.

(51) Int. Cl.
*A61K 38/00* (2006.01)
*A61K 39/00* (2006.01)
(52) U.S. Cl. .............. 514/18.7; 514/886; 424/185.1
(58) Field of Classification Search .......... None
See application file for complete search history.

(56) References Cited

U.S. PATENT DOCUMENTS

| 6,541,224 B2 | 4/2003 | Yu et al. |
| 2002/0107196 A1 | 8/2002 | Gupta |
| 2003/0069265 A1 | 4/2003 | Saxena et al. |
| 2003/0148940 A1 | 8/2003 | Tudan et al. |

FOREIGN PATENT DOCUMENTS

| WO | WO 2005/054493 | 6/2005 |
| WO | WO 2006/074464 | 7/2006 |

OTHER PUBLICATIONS

GenBank Accession No. NM_013655 dated Dec. 3, 2007, 4 pgs.
GenBank Accession No. NM_199168 dated Dec. 3, 2007, 5 pgs.
GenBank Accession No. NM_021704 dated Dec. 3, 2007, 4 pgs.
Akira et al., "Toll-like receptors: critical proteins linking innate and acquired immunity," *Nat. Immunol.*, 2001, 2(8):675-680.
Akira and Takeda, "Toll-Like Receptor Signalling," *Nat. Rev. Immunol.*, 2004, 4:499-511.
Yamada, "Extracellular Matrix," *Current Protocols in Cell Biology*, 2006, John Wiley, New York, NY, Chapter 10.
Broxmeyer et al., "Transgenic Expression of Stromal Cell-Derived Factor-1/CXC Chemokine Ligand 12 Enhances Myeloid Progenitor Cell Survival/Antiapoptosis In Vitro in Response to Growth Factor Withdrawal and Enhances Myelopoiesis In Vivo," *J. Immunol.*, 2003, 170:421-429.
Brunn et al., "Conditional signaling by Toll-like receptor 4," *FASEB J.*, published online Feb. 28, 2005, 16 pages.
Cardin and Weintraub, "Molecular Modeling of Protein-Glycosaminoglycan Interactions," *Arteriosclerosis*, 1989, 9:21-32.
Ceradini et al., "Progenitor cell trafficking is regulated by hypoxic gradients through HIF-1 induction of SDF-1," *Nature Medicine*, 2004, 10(8):858-864.
Conrad, "Degradation of Heparan Sulfate by Nitrous acid," *Methods in Molecular Biology*, 2001, 171:347-351.
Dempsey et al., "Heparanase expression in invasive trophoblasts and acute vascular damage," *Glycobiology*, 2000, 10(5):467-475.
Dunn, "Prevention and Treatment of Multiple Organ Dysfunction Syndrome: Lessons Learned and Future Prospects," *Surg. Infect.*, 2000, 1(3):227-237.
Eddleston et al., "Functional Expression of the C-X-C Chemokine Receptor CXCR4 by Human Bronchial Epithelial Cells: Regulation by Proinflammatory Mediators," *J. Immunol.*, 2002, 169:6445-6451.
Galanos et al., "Galactosamine-induced sensitization to the lethal effects of endotoxin," *Proc. Natl. Acad. Sci. USA*, 1979, 76(11):5939-5943.
Han et al., "Lysophosphatidylcholine up-regulates CXCR4 chemokine receptor expression in human CD4 T cells," *J. Leukoc. Biol.*, 2004, 76:195-202.
Hoffmann and Reichhart, "*Drosophila* innate immunity: an evolutionary perspective," *Nat. Immunol.*, 2002, 3(2):121-126.
Hulbert et al., "Resistance Gene Complexes: Evolution and Utilization," *Annu. Rev. Phytopathol.*, 2001, 39:285-312.
Ihrcke et al., "Regulation of Platelet Heparanase During Inflammation: Role of pH and Proteinases," *J. Cell. Physiol.*, 1998, 175:255-267.
Ihrcke and Platt, "Shedding of Heparan Sulfate Proteoglycan by Stimulated Endothelial Cells: Evidence for Proteolysis of Cell-Surface Molecules," *J. Cell. Physiol.*, 1996, 168:625-637.
Johnson et al., "Receptor-Mediated Monitoring of Tissue Well-Being Via Detection of Soluble Heparan Sulfate by Toll-Like Receptor 4," *J. Immunol.*, 2002, 168:5233-5239.
Kainulainen et al., "Syndecans, Heparan Sulfate Proteoglycans, Maintain the Proteolytic Balance of Acute Wound Fluids," *J. Biol. Chem.*, 1998, 273(19):11563-11569.
Kaisho and Akira, "Toll-like receptors as adjuvant receptors," *Biochim. Biophys. Acta*, 2002, 1589:1-13. Kishore et al., "Selective suppression of Toll-like receptor 4 activation by chemokine receptor 4," *FEBS Letters*, 2005, 579(3):699-704.
Kodaira et al., "Phenotypic and Functional Maturation of Dendritic Cells Mediated by Heparan Sulfate," *J. Immunol.*, 2000, 165:1599-1604.
Krutzik et al., "The role of Toll-like receptors in host defense against microbial infection," *Curr. Opin. Immunol.*, 2001, 13:104-108.
Magor and Magor, "Evolution of effectors and receptors of innate immunity," *Dev. Comp. Immunol.*, 2001, 25:651-682.
McKenzie et al., "Biochemical characterization of the active heterodimer form of human heparanase (Hpa1) protein expressed in insect cells," *Biochem. J.*, 2003, 373:423-435.

(Continued)

Primary Examiner — Christine J Saoud
Assistant Examiner — Jegatheesan Seharaseyon
(74) Attorney, Agent, or Firm — Casimir Jones, S.C.

(57) ABSTRACT

This description provides methods and materials related to modulating Toll-like receptor activity. For example, methods and materials for increasing or decreasing the responsiveness of a TLR4 polypeptide are provided.

4 Claims, 13 Drawing Sheets

OTHER PUBLICATIONS

Medzhitov and Janeway, Jr., "Decoding the Patterns of Self and Nonself by the Innate Immune System," *Science*, 2002, 296:298-300.

Netelenbos et al., "Proteoglycans on bone marrow endothelial cells bind and present SDF-1 towards hematopoietic progenitor cells," *Leukemia*, 2003, 17:175-184.

Okada et al., "Structural Recognition by Recombinant Human Heparanase That Plays Critical Roles in Tumor Metastasis. Hierarchical sulfate groups with differential effects and the essential target disulfated trisaccharide sequence," *J. Biol. Chem.*, 2002, 277(45):42488-42495.

Orsini et al., "Trafficking of the HIV coreceptor CXCR4: Role of arrestins and identification of residues in the C-terminal tail that mediate receptor internalization," *J. Biol. Chem.*, 2000, 274(43):31076-31086.

Paterson and Webster, "Sepsis and the systemic inflammatory response syndrome," *J.R. Coll. Surg. Edinb.*, 2000, 45:178-182.

Paya et al., "NF-κB-dependent induction of the NF-κB p50 subunit gene promoter underlies self-perpetuation of human immunodeficiency virus transcription in monocytic cells," *Proc. Natl. Acad. Sci. USA*, 1992, 89:7826-7830.

Petit et al., "G-CSF induces stem cell mobilization by decreasing bone marrow SDF-1 and up-regulating CXCR4," *Nat. Immunol.*, 2002, 3(7):687-694.

Platt et al., "Release of Heparan Sulfate from Endothelial Cells," *J. Exp. Med.*, 1990, 171:1363-1368.

Proudfoot, "Chemokine Receptors: Multifaceted Therapeutic Targets," *Nat. Rev. Immunol.*, 2002, 2:106-115.

Rao et al., "Elastase Release by Transmigrating Neutrophils Deactivates Endothelial-bound SDF-1α and Attenuates Subsequent T Lymphocyte Transendothelial Migration," *J. Exp. Med.*, 2004, 200(6):713-724.

Saadi et al., "Regional manifestations and control of the immune system," *FASEB J.*, 2002, 16:849-856.

Sotsios et al., "The CXC Chemokine Stromal Cell-Derived Factor Activates a $G_i$-Coupled Phosphoinositide 3-Kinase in T Lymphocytes," *J. Immunol.*, 1999, 163:5954-5963.

Squadrito et al., "Gene Transfer of IκBα Limits Infarct Size in a Mouse Model of Myocardial Ischemia-Reperfusion Injury," *Laboratory Investigation*, 2003, 83(8):1097-1104.

Takeda et al., "Toll-Like Receptors," *Annu. Rev. Immunol.*, 2003, 21:335-376.

Triantafilou and Triantafilou, "Lipopolysaccharide recognition: CD14, TLRs and the LPS-activation cluster," *Trends Immunol.*, 2002, 23(6):301-304.

Triantafilou et al., "Mediators of innate immune recognition of bacteria concentrate in lipid rafts and facilitate lipopolysaccharide-induced cell activation," *J. Cell Sci.*, 2002, 115:2603-2611.

Wright et al., "Transforming growth factor-β1 down-regulates expression of chemokine stromal cell-derived factor-1: functional consequences in cell migration and adhesion," *Blood*, 2003, 102(6):1978-1984.

Ye, "Regulation of nuclear factor κB activation by G-protein-coupled receptors," *J. Leukoc. Biol.*, 2001, 70:839-848.

Triantafilou et al., "A CD14-independent LPS receptor cluster," Nature Immunology, 2001, 2:338-345.

Figure 10

GCCGCACTTTCACTCTCCGTCAGCCGCATTGCCCGCTCGGCGTCCGGCCCCGAC
CCGCGCTCGTCCGCCCGCCCGCCCGCCCGCCCGCGCCATGAACGCCAAGGTCGTG
GTCGTGCTGGTCCTCGTGCTGACCGCGCTCTGCCTCAGCGACGGGAAGCCCGTCA
GCCTGAGCTACAGATGCCCATGCCGATTCTTCGAAAGCCATGTTGCCAGAGCCAA
CGTCAAGCATCTCAAAATTCTCAACACTCCAAACTGTGCCCTTCAGATTGTAGCC
CGGCTGAAGAACAACAACAGACAAGTGTGCATTGACCCGAAGCTAAAGTGGATT
CAGGAGTACCTGGAGAAAGCTTTAAACAAGTAAGCACAACAGCCAAAAAGGACT
TTCCGCTAGACCCACTCGAGGAAAACTAAAACCTTGTGAGAGATGAAAGGGCAA
AGACGTGGGGGAGGGGGCCTTAACCATGAGGACCAGGTGTGTGTGGGGTGGG
CACATTGATCTGGGATCGGGCCTGAGGTTTGCCAGCATTTAGACCCTGCATTTAT
AGCATACGGTATGATATTGCAGCTTATATTCATCCATGCCCTGTACCTGTGCACG
TTGGAACTTTTATTACTGGGGTTTTTCTAAGAAAGAAATTGTATTATCAACAGCA
TTTTCAAGCAGTTAGTTCCTTCATGATCATCACAATCATCATCATTCTCATTCTCA
TTTTTTAAATCAACGAGTACTTCAAGATCTGAATTTGGCTTGTTTGGAGCATCTCC
TCTGCTCCCTGGGGAGTCTGGGCACAGTCAGGTGGTGGCTTAACAGGGAGCTG
GAAAAAGTGTCCTTTCTTCAGACACTGAGGCTCCCGCAGCAGCGCCCCTCCCAAG
AGGAAGGCCTCTGTGGCACTCAGATACCGACTGGGGCTGGGCGCCGCCACTGCC
TTCACCTCCTCTTTCAACCTCAGTGATTGGCTCTGTGGGCTCCATGTAGAAGCCAC
TATTACTGGGACTGTGCTCAGAGACCCCTCTCCCAGCTATTCCTACTCTCTCCCCG
ACTCCGAGAGCATGCTTAATCTTGCTTCTGCTTCTCATTTCTGTAGCCTGATCAGC
GCCGCACCAGCCGGGAAGAGGGTGATTGCTGGGGCTCGTGCCCTGCATCCCTCTC
CTCCCAGGGCCTGCCCCACAGCTCGGGCCCTCTGTGAGATCCGTCTTTGGCCTCC
TCCAGAATGGAGCTGGCCCTCTCCTGGGGATGTGTAATGGTCCCCCTGCTTACCC
GCAAAAGACAAGTCTTTACAGAATCAAATGCAATTTTAAATCTGAGAGCTCGCTT
TGAGTGACTGGGTTTTGTGATTGCCTCTGAAGCCTATGTATGCCATGGAGGCACT
AACAAACTCTGAGGTTTCCGAAATCAGAAGCGAAAAAATCAGTGAATAAACCAT
CATCTTGCCACTACCCCCTCCTGAAGCCACAGCAGGGTTTCAGGTTCCAATCAGA
ACTGTTGGCAAGGTGACATTTCCATGCATAAATGCGATCCACAGAAGGTCCTGGT
GGTATTTGTAACTTTTGCAAGGCATTTTTTATATATATTTTGTGCACATTTTTT
TTTACGTTTCTTTAGAAAACAAATGTATTTCAAAATATATTTATAGTCGAACAATT
CATATATTTGAAGTGGAGCCATATGAATGTCAGTAGTTTATACTTCTCTATTATCT
CAAACTACTGGCAATTTGTAAAGAAATATATATGATATATAAATGTGATTGCAGC
TTTTCAATGTTAGCCACAGTGTATTTTTTCACTTGTACTAAAATTGTATCAAATGT
GACATTATATGCACTAGCAATAAAATGCTAATTGTTTCATGGTATAAACGTCCTA
CTGTATGTGGGAATTTATTTACCTGAAATAAAATTCATTAGTTGTTAGTGATGGA
GCTTAAAAAAAA (SEQ ID NO:1)

Figure 11

GACCACTTTCACTCTCGGTCCACCTCGGTGTCCTCTTGCTGTCCAGCTCTGCAGCC
TCCGGCGCGCCCTCCCGCCCACGCCATGGACGCCAAGGTCGTCGCCGTGCTGGCC
CTGGTGCTGGCCGCGCTCTGCATCAGTGACGGTAAACCAGTCAGCCTGAGCTACC
GATGCCCCTGCCGGTTCTTCGAGAGCCACATCGCCAGAGCCAACGTCAAGCATCT
GAAAATCCTCAACACTCCAAACTGTGCCCTTCAGATTGTTGCACGGCTGAAGAAC
AACAACAGACAAGTGTGCATTGACCCGAAATTAAAGTGGATCCAAGAGTACCTG
GAGAAAGCTTTAAACAAGTAAGCACAACAGCCCAAAGGACTTTCCAGTAGACCC
CCGAGGAAGGCTGACATCCGTGGGAGATGCAAGGGCAGTGGTGGGGAGGAGGG
CCTGAACCCTGGCCAGGATGGCCGGCGGGACAGCACTGACTGGGGTCATGCTAA
GGTTTGCCAGCATAAAGACACTCCGCCATAGCATATGGTACGATATTGCAGCTTA
TATTCATCCCTGCCCTCGCCCGTGCACAATGGAGCTTTATAACTGGGGTTTTCT
AAGGAATTGTATTACCCTAACCAGTTAGCTTCATCCCCATTCTCCTCATCCTCATC
TTCATTTTAAAAAGCAGTGATTACTTCAAGGGCTGTATTCAGTTTGCTTTGGAGCT
TCTCTTTGCCCTGGGGCCTCTGGGCACAGTTATAGACGGTGGCTTTGCAGGGAGC
CCTAGAGAGAAACCTTCCACCAGAGCAGAGTCCGAGGAACGCTGCAGGGCTTGT
CCTGCAGGGGCGCTCCTCGACAGATGCCTTGTCCTGAGTCAACACAAGATCCGG
CAGAGGGAGGCTCCTTTATCCAGTTCAGTGCCAGGGTCGGGAAGCTTCCTTTAGA
AGTGATCCCTGAAGCTGTGCTCAGAGACCCTTTCCTAGCCGTTCCTGCTCTCTGCT
TGCCTCCAAACGCATGCTTCATCTGACTTCCGCTTCTCACCTCTGTAGCCTGACGG
ACCAATGCTGCAATGGAAGGGAGGAGAGTGATGTGGGGTGCCCCCTCCCTCTCTT
CCCTTTGCTTTCCTCTCACTTGGGCCCTTTGTGAGATTTTTCTTTGGCCTCCTGTAG
AATGGAGCCAGACCATCCTGGATAATGTGAGAACATGCCTAGATTTACCCACAA
AACACAAGTCTGAGAATTAATCATAAACGGAAGTTTAAATGAGGATTTGGACTTT
GGTAATTGTCCCTGAGTCCTATATATTTCAACAGTGGCTCTATGGGCTCTGATCG
AATATCAGTGATGAAAATAATAATAATAATAATAACGAATAAGCCAGAATC
TTGCCATGAAGCCACAGTGGGGATTCTGGGTTCCAATCAGAAATGGAGACAAGA
TAAAACTTGCATACATTCTTATGATCACAGACGGCCCTGGTGGTTTTGGTAACT
ATTTACAAGGCATTTTTTACATATATTTTGTGCACTTTTTATGTTTCTTTGGAAG
ACAAATGTATTTCAGAATATATTTGTAGTCAATTCATATATTTGAAGTGGAGCCA
TAGTAATGCCAGTAGATATCTCTATGATCTTGAGCTACTGGCAACTTGTAAAGAA
ATATATATGACATATAAATGTATTGTAGCTTTCCGGTGTCAGCCACGGTGTATTTT
TCCACTTGGAATGAAATTGTATCAACTGTGACATTATATGCACTAGCAATAAAAT
GCTAATTGTTTCATGCTGTAAACCTCCTACCGTATGTGGGAATTTATTTACCTGAA
ATAAAATCTACTAGTTGTT (SEQ ID NO:2)

Figure 12

GACCACTTTCACTCTCGGTCCACCTCGGTGTCCTCTTGCTGTCCAGCTCTGCAGCCTCCGGCGCGCC
CTCCCGCCCACGCCATGGACGCCAAGGTCGTCGCCGTGCTGGCCCTGGTGCTGGCCGCGCTCTGCA
TCAGTGACGGTAAACCAGTCAGCCTGAGCTACCGATGCCCCTGCCGGTTCTTCGAGAGCCACATCG
CCAGAGCCAACGTCAAGCATCTGAAAATCCTCAACACTCCAAACTGTGCCCTTCAGATTGTTGCAC
GGCTGAAGAACAACAACAGACAAGTGTGCATTGACCCGAAATTAAAGTGGATCCAAGAGTACCTG
GAGAAAGCTTTAAACAAGAGGCTCAAGATGTGAGAGGTGTGAGTCAGACGCCCGAGGAACTTACA
GGAGGAGCCTAGGTCTGAAGTCAGTGTTAGGGAAGGGCCCATAGCCACTTCCTCTGCTCCTGAGC
AGGGCTGAAGCCGTTTGCAAGGGACTTGCTTTGCACAGTTTTGCTGTACTTTCACATTTTATTATGT
AGCAAGATACATGGTGATTTTTTTTTTTTTCATTTAGCCTGATTTTCCAACGTCATTGGTGACAGG
CCAAGGCCACTATGTTATTTCCTTTGTTCTGGTATCCTTCCCTTGGAGGACCTTCTCTGAGTAGTGG
CTCCCCAGGTTTGTCCTTTGAGCTGAGGCAGGAGGCTCACCCATTCTTCTGAATAGGAACTGGGTG
TTCCCACCCCCCAAGGACTGCAGGGCTTTCCCAAGCTGAGGCAGGAACGTGAGGCCAGGGAAGAG
TGAGCTTCACCCTCATCCCACGCTGTCCTCCTCAACCCACCATGCTCATCATTCTGTCTCATCCATC
CATCCATCCATCCATTCATCGCCATGTGTCCGCAAGACTGTCTCCATGACCCTGAAAAAGGACTCT
CGAGATGAAATCCTTTATTCAAATGGGACAGCAAGAAGGAAAAGCCAATGTCTGGTGTCTCTCCC
CCCGCCCCTACCCTGCGCGCATCTATGTCTTGTTTGGAATATTGTCTCTTCAACCCCCTGTTCATGT
CCTTCTCACTCATGATCGATGTCTTGTCTGTGCACTGTCTCTAACCCAAATGCAAAGGCTGAGTGTG
AGGTGATGGCCCCGAGGTCCAGGTTGTAGTCATGGAAAGAGCCCTGCTGTCTCCCTTCTCAGGGGG
CCCATTTTAGACACACAAAGCCCAAAGAAAGGTGGTTTGCAACAGTGCTTAGCTCGAGCCTCCATA
TTTCCATAACTGTTAGCTTAAAACTGTGGGGTTTTACCTTCCTGGAACCAAATGCATTCTTCTGTTG
AGGAGTAACAGGTCTCAATTCTTTTCAATTAATTTTAAAAGTCAATCACTAAGAGCATCGGCTTTG
GGCCCTGATGGGCAGGCATTTCCCTGGAAGGGGGTGAACTACCTACCTCTCCTCAAGACAGCCG
AAGGGTGGGATTGGTGCCGCTCTGGGAAGCGTGGCCCCAGGAGTTTTGTCCTCTGCAGTTTTTAAT
GCAAGTTCACTGCCACTTTGACAAAAGCCCAATTAGAAGCCAGTCTCTAGTTCCTTAAACAAAACA
GACAGAGTAAGGAAAGGAAGGAGGGTGGCAGCCAGCTGGCTGGACACTCGAGAAAGACGGGGAA
GTAAGCTACAGAAAGATAGTCTTCAAAAACAGGTGTTTGAGAGTGAATACTCTGTAGAATTGTTA
GTGGGGTGTGTGTGGTGGTGGTGGGGGGATTTCTACAAAATAGTCCTTTAAGTTGAGTTTACAGCA
GATGAAAAATCCAACCAGCAAAATTTTGATCAAATTTGAACAAAAACCCAAAAACCTAAAACTGT
TGAGCAGGTTGCGATGAGGAGCACAGGGCTAGCTGCAGAGCTGGATCCTCAGGAGGATAGCGAAT
TATTTTCAACCCTGGAATAGAAACCACACACTGGCTTGCTGTGCACCAGCCACTTTGCATCTAATC
CAAGCTTTGAAGGGTGTTGCTTGGGAGGAAACAAATACAGCCTTCCATCTTCACTCCAGTTAGGGA
TCCTTTCAAAGTCTCCTTCACAGTGAGGAAAAAGAGAAGGGTAGAAACTTTAGGGAGCCGGATTT
GTGTATCAATTCCTCCGCTGACAGTCAGTTTCTAGATGGAGACAGCCTGCTTAAAGCAAATCCGAA
TTTAAATAGGACATTTACATCGGAAAAGTCTCTCCCTACCTTAATCCCCCATTCTCTTGCTTTCAAA
ATACAAGCACAGCAGTCCTTGAATGGCTGTTGACCCAGGGCACCTAGCTGTCCCTGCTGGTCCTGG
GGCTGCCAGAATTCCCTTGGGCGCCAAGCAACCTGCCAGGTAGCCAGTCCCTCTGTTACAAGCCTT
TGCATCTGGATAGGGAAAGGGGTGGAGACATACAGTCTGCTTTGTGTTGAAACCCAGATTTGTACC
CTGTGTTTATACACTGCTGCTGGCTCCCGAGGACAGTGGGACTTTAGCAAGGAAGTGCAGCCGAG
GGGTAAAGAGCCCTCTGGTTCATTGCCTGATCGGCTTTGAGAGAGGGTTTGGAGGGCAAGGGGCT
GCATTCCTCTGAGGGACTTGGCCTGAGGCCTTTCGGGCCTCTCCAGTGGGTTCTGTTTATCCTCTCA
TGGGTGATTATCTCAGTGGTGTCACCAGGGGCTTCCTCCCAGAAGTCAGTCATCCCCAGGCCGTGC
ACCCTTTTCAGCTGGATGAGAGCCAGGGATGCATTCTCTCCAAACAGCTACCCTGGCCCATTTTAA
GGTAATCTCATTCTTCAAAATGTTCCATAGAATCCTCCAAATTCCCCAGCAGACTTCTACCCTCGC
CAAGTTCCCAAAACCCACTCAGCAAAGTTGCCAACCTCGACGGGCTAGCAGTGTCTAAGCAGCGA
TGGGTTCAGTGTTGTGTGTGGTGAATACTGTATTTTGTTTCAGTTCTGTCTCCCAGATAATGTGAAA
ACGGTCCAGGAGAAGGCAGCTTCCTATATGCAGCGTGTGCTTTCTTATTCTTATTTTTAATATATGA
CAGTTATTTGAGAAGCCATTTCTACTTTGAAGTCATTATCGATGAAAGTGATGTATCTTCACCTACC
ATTTTCCTAATAAAGTTCTGTATTCAAATAT (SEQ ID NO:3)

MODULATING TOLL-LIKE RECEPTOR ACTIVITY

CROSS-REFERENCE TO RELATED APPLICATIONS

This application is a National Stage application under 35 U.S.C. §371 and claims benefit under 35 U.S.C. §119(a) of International Application No. PCT/US2006/000864 having an International Filing Date of Jan. 10, 2006, which claims the benefit of U.S. Provisional Application Ser. No. 60/642,872, filed Jan. 10, 2005.

STATEMENT AS TO FEDERALLY SPONSORED RESEARCH

This invention was made with government support under HL046810 and AI053733 awarded by the National Institutes of Health. The government has certain rights in the invention.

BACKGROUND

1. Technical Field

This description relates to methods and materials involved in modulating (e.g., increasing or decreasing) Toll-like receptor activity.

2. Background Information

The Toll family of polypeptides is remarkably conserved across the taxonomic kingdoms. This family includes the invertebrate Toll polypeptides, the vertebrate Toll-like receptors, and the plant resistance genes (Hoffmann and Reichhart, (2002) *Nat. Immunol.*, 3:121-126; Akira et al., (2001) *Nat. Immunol.*, 2:675-680; and Hulbert et al., (2001) *Annu. Rev. Phytopathol.*, 39:285-312). Many of these polypeptides have homologous domains and signaling pathways, which are used to trigger inflammatory and immunological responses. However, the function of these proteins extends beyond host defense.

As expressed on leukocytes, endothelial cells, and various parenchymal cells, Toll-like receptor 4 (TLR4) detects the products of microorganisms, such as lipopolysaccharide (LPS), and endogenous substances, such as heparan sulfate and hyaluronic acid. Following detection of these substances, TLR4 transduces signals leading to activation of NFκB, among other signaling pathways (Takeda et al., *Annu. Rev. Immunol.*, 21:335-376 (2003)), that induce the expression of genes that incite inflammation and adaptive immunity. These responses sequester and clear microorganisms and heighten resistance of the host upon re-infection (Akira et al., *Nat. Immunol.*, 2:675-680 (2001) and Krutzik et al., *Curr. Opin. Immunol.*, 13:104-108 (2001)).

SUMMARY

This description involves methods and materials for modulating (e.g., increasing or decreasing) Toll-like receptor activity. As described herein, CXCR4 binding agents (e.g., anti-CXCR4 antibodies and CXCR4 ligands) can be used to modulate the ability of Toll-like receptors to respond to Toll-like receptor agonists. For example, an anti-CXCR4 antibody can interact with a CXCR4 polypeptide such that the activity of a TLR4 polypeptide in response to a TLR4 agonist (e.g., LPS) is increased as compared to the activity observed when a CXCR4 polypeptide is not contacted with an anti-CXCR4 antibody. In addition, a CXCR4 agonist (e.g., an SDF-1 polypeptide) can interact with a CXCR4 polypeptide such that the activity of a TLR4 polypeptide in response to a TLR4 agonist (e.g., LPS) is decreased as compared to the activity observed when a CXCR4 polypeptide is not contacted with a CXCR4 agonist. In some embodiments, the ability of Toll-like receptors to respond to a Toll-like receptor agonist can be modulated by increasing or decreasing the expression of a CXCR4 polypeptide. For example, a nucleic acid molecule designed to transcribe siRNA molecules capable of reducing the expression of a CXCR4 polypeptide can be introduced into cells expressing a TLR4 polypeptide such that the activity of the TLR4 polypeptide in response to a TLR4 agonist (e.g., LPS) is increased as compared to the activity observed in control cells lacking the nucleic acid molecule. In addition, a nucleic acid molecule designed to express a CXCR4 polypeptide can be introduced into cells expressing a TLR4 polypeptide such that the activity of the TLR4 polypeptide in response to a TLR4 agonist (e.g., LPS) is decreased as compared to the activity observed in control cells lacking the nucleic acid molecule.

Modulating Toll-like receptors by targeting the activity or expression of a CXCR4 polypeptide provides an effective way to either increase or decrease Toll-like receptor responses. By increasing the responsiveness of Toll-like receptors, one can increase a mammal's ability to respond to foreign agents (e.g., microorganisms). In some cases, the methods and materials provided herein for increasing the responsiveness of Toll-like receptors can be used to increase a mammal's ability to respond to a vaccine. By decreasing the responsiveness of Toll-like receptors, one can decrease the level of a mammal's immune response. For example, the methods and materials provided herein for decreasing the responsiveness of Toll-like receptors can be used to reduce the severity of sepsis, inflammation, or autoimmune conditions within a mammal.

In general, this description features a method for increasing or decreasing Toll-like receptor activation in cells, wherein the cells are in the presence of a Toll-like receptor agonist. The method includes administering a CXCR4 binding agent to the cells under conditions wherein the level of the Toll-like receptor activation in the cells is increased or decreased. The Toll-like receptor can be TLR-4. The cells can be leukocytes, endothelial cells, or parenchymal cells. The Toll-like receptor agonist can be LPS. The CXCR4 binding agent can be a CXCR4 agonist, and the level of the Toll-like receptor activation in the cells can be decreased. The CXCR4 agonist can be an SDF-1 polypeptide. The CXCR4 binding agent can be a CXCR4 antagonist, and the level of the Toll-like receptor activation in the cells can be increased. The CXCR4 antagonist can be an anti-CXCR4 antibody. The method can include detecting the increase or decrease in the level of the Toll-like receptor activation. The cells can be in vitro. The cells can be in a mammal (e.g., a human). The method can include administering the Toll-like receptor agonist to a mammal or to a cell culture to form the cells. The method can include exposing the cells or a mammal containing the cells to conditions that induce the presence of the Toll-like receptor agonist.

In another embodiment, this description features a method for increasing or decreasing a cell's ability to be activated by a Toll-like receptor agonist. The method includes administering a CXCR4 binding agent to a cell under conditions wherein the cell, when contacted with the Toll-like receptor agonist, contains an increased or decreased level of Toll-like receptor activation. The Toll-like receptor can be TLR-4. The cells can be leukocytes, endothelial cells, or parenchymal cells. The Toll-like receptor agonist can be LPS. The CXCR4 binding agent can be a CXCR4 agonist, and the level of the Toll-like receptor activation in the cell, when contacted with the Toll-like receptor agonist, can be decreased. The CXCR4 agonist can be an SDF-1 polypeptide. The CXCR4 binding agent can be a CXCR4 antagonist, and the level of the Toll-like receptor activation in the cell, when contacted with the Toll-like receptor agonist, can be increased. The CXCR4 antagonist can be an anti-CXCR4 antibody. The method can include detecting the increase or decrease in the level of the Toll-like receptor activation. The cell can be in vitro. The cell can be in a mammal (e.g., a human). The cell can be contacted with the Toll-like receptor agonist after the CXCR4 binding agent is administered to the cell. The cell can be contacted with the Toll-like receptor agonist before the CXCR4 binding agent is administered to the cell. The method can include administering the Toll-like receptor agonist to a mammal containing the cell or to a cell culture containing the cell after the CXCR4 binding agent is administered to the cell. The method can include administering the Toll-like receptor agonist to a mammal containing the cell or to a cell culture containing the cell before the CXCR4 binding agent is administered to the cell.

In another embodiment, this description features a method for increasing or decreasing a cell's ability to be activated by a Toll-like receptor agonist. The method includes increasing or decreasing expression of a CXCR4 polypeptide in a cell, wherein an increase in the expression decreases the ability of the cell to be activated by the Toll-like receptor agonist, and wherein a decrease in the expression increases the ability of the cell to be activated by the Toll-like receptor agonist. The Toll-like receptor can be TLR-4. The cells can be leukocytes, endothelial cells, or parenchymal cells. The Toll-like receptor agonist can be LPS. The method can include introducing a nucleic acid molecule encoding the CXCR4 polypeptide into the cell, and the nucleic acid molecule can express the CXCR4 polypeptide in the cell. The method can include introducing a nucleic acid molecule capable of expressing an siRNA molecule containing a sequence complementary to a sequence of an mRNA encoding the CXCR4 polypeptide, and the nucleic acid molecule can express the siRNA molecule in the cell. The method can include detecting the increase or decrease in the ability to be activated by the Toll-like receptor agonist. The cell can be in vitro. The cell can be in a mammal (e.g., a human). The cell can be contacted with the Toll-like receptor agonist after the expression of the CXCR4 polypeptide is increased or decreased in the cell. The cell can be contacted with the Toll-like receptor agonist before the expression of the CXCR4 polypeptide is increased or decreased in the cell. The method can include administering the Toll-like receptor agonist to a mammal containing the cell or to a cell culture containing the cell after the CXCR4 binding agent is administered to the cell. The method can include administering the Toll-like receptor agonist to a mammal containing the cell or to a cell culture containing the cell before the CXCR4 binding agent is administered to the cell.

In another embodiment, this description features a method for reducing inflammation within a mammal. The method can include administering a CXCR4 agonist to the mammal under conditions wherein the level of inflammation in the mammal is reduced. The mammal can have an inflammatory condition (e.g., systemic inflammatory response syndrome, sepsis, pancreatitis, adult respiratory distress syndrome, or asthma). The method can include identifying the mammal as having an inflammatory condition prior to the administration. The level of the inflammation in the mammal can be determined after the administration. The CXCR4 agonist can be an SDF-1 polypeptide.

In another embodiment, this description features a method for treating a mammal having a condition selected from the group consisting of sepsis, an ischemia-reperfusion injury, obesity, osteoporosis, systemic inflammatory response syndrome, pancreatitis, adult respiratory distress syndrome, and asthma. The method includes administering a CXCR4 agonist to the mammal under conditions wherein the severity of a symptom of the condition is reduced. The mammal can have sepsis. The method can include identifying the mammal as having the condition prior to the administration. The severity of the symptom can be determined after the administration. The CXCR4 agonist can be an SDF-1 polypeptide.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF DRAWINGS

FIG. 10 is a listing of a nucleic acid sequence for a human SDF-1 polypeptide.

FIG. 11 is a listing of a nucleic acid sequence for a mouse SDF-1 variant 1 polypeptide.

FIG. 12 is a listing of a nucleic acid sequence for a mouse SDF-1 variant 2 polypeptide.

DETAILED DESCRIPTION

Figure 1:
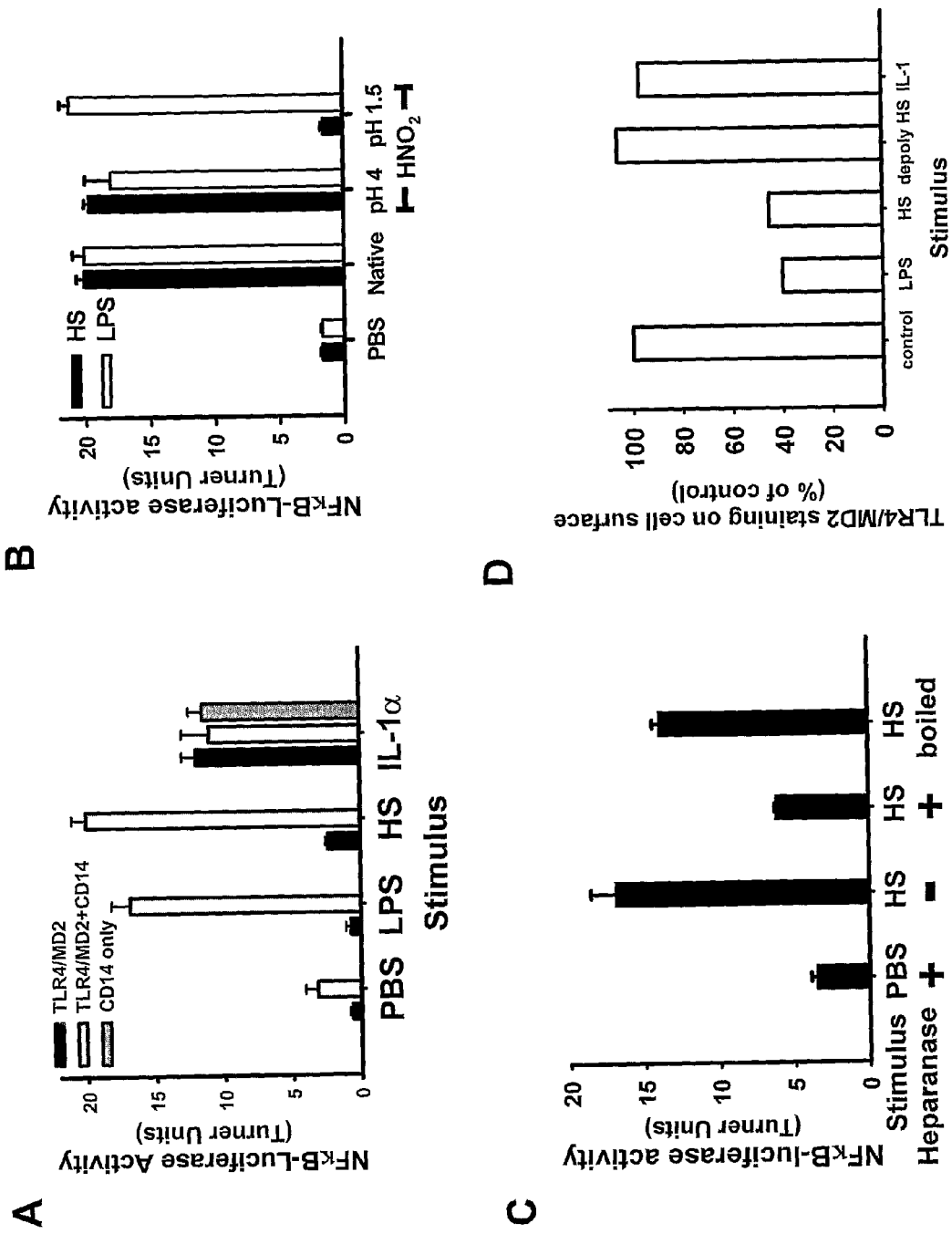
FIG. 1. Activation of TLR4 in HEK 293 cells. HEK 293 cells were stably transfected with expression vectors encoding murine TLR4 and MD2 (TLR4/MD2) or TLR4, MD2, and CD14 and tested for responses to TLR4 activators. (A) HEK 293 cell responses to TLR4 activators. HEK 293 cells stabily expressing TLR4 and MD2 and/or CD14 were transfected with NFκB-luciferase and internal control Renilla-luciferase reporter plasmids and tested for responses to 10 μg/mL of heparan sulfate or 10 ng/mL of LPS or recombinant human IL-1α. Response was measured by NFκB-activated luciferase expression measured 6 hours after stimulation. Cells expressing TLR4, MD2, and CD14 (HEK/TLR4(+) cells) respond to heparan sulfate and LPS. (B) Activation of TLR4 by agonists treated with nitrous acid. To test the specificity heparan sulfate activation of TLR4, HEK/TLR4(+) cells were transfected with NFκB- and control-luciferase reporter plasmids and then stimulated with intact heparan sulfate (10 μg/mL) or LPS (10 ng/mL) (Native), or with heparan sulfate or LPS that had been treated with nitrous acid ($HNO_2$) at pH 4.0 (cleaves heparan sulfate at unmodified glucosamine residues) or pH 1.5 (cleaves heparan sulfate at sulfated glucosamines). Controls were treated with the PBS vehicle. NFκB-luciferase activity was measured six hours after stimulating the cells with the indicated form of the activator. (C) Activation of TLR4 by heparan sulfate treated with heparanase. HEK/TLR4(+) were stimulated for 6 hours with 10 μg/mL of intact heparan sulfate (HS) or with HS digested with heparanase, which cleaves heparan sulfate adjacent to sulfated domains. Control HEK/TLR4(+) cells were stimulated with heparan sulfate treated with inactive enzyme (boiled) or control buffer. NFκB-luciferase activity was measured six hours after stimulating the cells with the indicated form of the activator. (D) Effect of TLR4 agonists on cell surface expression of TLR4/MD2. HEK/TLR4(+) cells were stimulated with 10 μg/mL of heparan sulfate or depolymerized heparan sulfate (nitrous acid, pH 1.5) or with 10 ng/mL of LPS, or recombinant human IL-1α, as positive and negative controls. Six hours later expression of TLR4 on the cell surface was determined by flow cytometry using a monoclonal antibody specific the TLR4/MD2 complex. TLR4 signaling was the mean of determination in triplicate wells and is representative of three separate experiments. These results illustrate that HEK/TLR4(+) cells are activated specifically by LPS or intact heparan sulfate, but not by heparan sulfate that is depolymerized by low pH nitrous acid or by heparanase, which cleave heparan sulfate at highly sulfated regions of the polysaccharide.

This description provides methods and materials related to modulating Toll-like receptor activity. For example, CXCR4 binding agents can be used to modulate the ability of Toll-like receptors to respond to Toll-like receptor agonists. The term "CXCR4 binding agent" as used herein includes any molecule that interacts with a CXCR4 polypeptide. Examples of CXCR4 binding agents include, without limitation, natural ligands for a CXCR4 polypeptide (e.g., an SDF-1 polypeptide), synthetic agonists and antagonists of a CXCR4 polypeptide (e.g., small molecule agonists and antagonists of a CXCR4 polypeptide), anti-CXCR4 antibodies (e.g., monoclonal antibodies, antibody fragments, and humanized antibodies capable of binding a CXCR4 polypeptide), and non-signaling ligands for a CXCR4 polypeptide (e.g., a non-signaling SDF-1 polypeptide and SDF-1 homologues).

Any method can be used to identify, obtain, or administer a CXCR4 binding agent. For example, the methods and materials described elsewhere can be used to identify, obtain, or administer a CXCR4 binding agent (See, e.g., U.S. Patent Application Publication US 2002/0107196 A1; U.S. Patent Application Publication US 2003/0148940 A1; and U.S. Patent Application Publication US 2003/0069265 A1). In some embodiments, the methods and materials described in PCT/US2004/018859 can be used to identify, obtain, or administer a CXCR4 binding agent. For example, a library of compounds can be screened for the ability to inhibit Toll-like receptor activity using any of the in vitro or in vivo methods provided in PCT/US2004/018859. Compounds identified as having the ability to inhibit Toll-like receptor activity then can be tested for the ability to bind a CXCR4 polypeptide.

The methods and materials provided herein can be used to modulate the responsiveness of any type of Toll-like receptor including, without limitation, a TLR1 polypeptide, a TLR2 polypeptide, a TLR3 polypeptide, a TLR4 polypeptide, a TLR5 polypeptide, a TLR6 polypeptide, a TLR7 polypeptide, a TLR8 polypeptide, a TLR9 polypeptide, or a TLR10 polypeptide. See, also, Akira and Takada, *Nature Reviews Immunology*, (4):499-511 (2004). In addition, the methods and materials provided herein can be used to modulate the ability of a Toll-like receptor to respond to any type of Toll-like receptor agonist including, without limitation, LPS, heparan sulfate, heat shock proteins (e.g., bacterial or endogenous heat shock proteins), hyaluronic acid, fibronectin fragments, fibrinogen fragments, viral fusion polypeptides, viral envelope polypeptides, and viral nucleic acids (e.g., double-stranded RNA).

In some embodiments, a CXCR4 binding agent capable of blocking the function of a CXCR4 polypeptide (e.g., an anti-CXCR4 antibody) can be administered to cells expressing a CXCR4 polypeptide and a Toll-like receptor polypeptide (e.g., a TLR4 polypeptide). In these cases, the CXCR4 binding agent can interact with the CXCR4 polypeptide such that the responsiveness of the TLR4 polypeptide to a TLR4 agonist (e.g., LPS) is increased as compared to the responsiveness observed when control cells are not contacted with the CXCR4 binding agent.

In other embodiments, a CXCR4 binding agent capable of acting as a CXCR4 agonist (e.g., a SDF-1 polypeptide) can be administered to cells expressing a CXCR4 polypeptide and a Toll-like receptor polypeptide (e.g., a TLR4 polypeptide). In these cases, the CXCR4 binding agent can interact with the CXCR4 polypeptide such that the responsiveness of the TLR4 polypeptide to a TLR4 agonist (e.g., LPS) is decreased as compared to the responsiveness observed when control cells are not contacted with the CXCR4 binding agent.

Any method can be used to administer a CXCR4 binding agent to cells. For example, a CXCR4 binding agent can be administered directly to cells in culture or can be administered to a mammal. In some cases, a CXCR4 binding agent can be administered to cells indirectly. For example, a nucleic acid molecule can be (1) designed to express a CXCR4 binding agent and (2) administered to cells in vitro or in vivo. In these cases, the nucleic acid can be designed to express, for example, an anti-CXCR4 antibody or an SDF-1 polypeptide. See, e.g., Broxmyer et al., *J. Immunology,* 170(1):421-9 (2003).

The responsiveness of a Toll-like receptor can be modulated by decreasing or increasing the expression level of a CXCR4 polypeptide. For example, molecules capable of reducing the expression of a CXCR4 polypeptide can be administered to cells that express a Toll-like receptor polypeptide (e.g., a TLR4 polypeptide) such that the expression of the CXCR4 polypeptide is reduced. In these cases, the reduced expression of a CXCR4 polypeptide can increase the responsiveness of a Toll-like receptor to a Toll-like receptor agonist (e.g., LPS) as compared to the responsiveness observed with control cells not treated with the molecule capable of reducing the expression of a CXCR4 polypeptide. Any type of molecule can be used to reduce the expression of a CXCR4 polypeptide including, without limitation, antisense molecules, ribozymes, DNAzymes, siRNA molecules, PNA molecules, and nucleic acid constructs designed to express one or more antisense molecules, ribozymes, DNAzymes, or siRNA molecules. For example, an siRNA molecule designed to reduce the expression of a human CXCR4 polypeptide can be administered to a human such that the responsiveness of a TLR4 polypeptide to a TLR4 agonist (e.g., LPS) is increased.

In another example, molecules capable of increasing the expression of a CXCR4 polypeptide can be administered to cells that express a Toll-like receptor polypeptide (e.g., a TLR4 polypeptide) such that the expression of the CXCR4 polypeptide is increased. In these cases, the increased expression of a CXCR4 polypeptide can decrease the responsiveness of a Toll-like receptor to a Toll-like receptor agonist (e.g., LPS) as compared to the responsiveness observed with control cells not treated with the molecule capable of increasing the expression of a CXCR4 polypeptide. Any type of molecule can be used to increase the expression of a CXCR4 polypeptide including, without limitation, nucleic acid constructs designed to express a CXCR4 polypeptide. For example, a viral vector designed to express a human CXCR4 polypeptide can be administered to a human such that the responsiveness of a TLR4 polypeptide to a TLR4 agonist (e.g., LPS) is decreased.

In each case, the cells can be in culture or in vivo. For example, a CXCR4 binding agent can be administered to a mammal such that cells expressing a CXCR4 polypeptide and a Toll-like receptor polypeptide exhibit an increased responsiveness to a TLR4 agonist such as LPS. The mammal can be any type of mammal including, without limitation, a rat, mouse, dog, cat, horse, cow, pig, sheep, goat, monkey, or human. In some cases, the mammal can be a mammal identified as needing, or for which it would be desirable to have, increased Toll-like receptor responsiveness such as, for example, (1) a mammal suffering from cancer, a tumor, microbial infection, an immunodeficiency (e.g., an HIV infection), or any combination thereof or (2) a mammal receiving a vaccine. For example, a mammal to be vaccinated can be treated as described herein to increase Toll-like receptor responsiveness prior to, concurrently with, or subsequent to a vaccination treatment. In other cases, the mammal can be a mammal identified as needing, or for which it would be desirable to have, decreased Toll-like receptor responsiveness such as, for example, a mammal suffering from inflammation, sepsis, an ischemia-reperfusion injury, obesity, osteoporosis, systemic inflammatory response syndrome, pancreatitis, adult respiratory distress syndrome, asthma, or any combination thereof.

As described herein, a ligand for a CXCR4 polypeptide can be used to reduce the responsiveness of a Toll-like receptor. One such ligand is an SDF-1 polypeptide. The human and two forms of murine SDF-1 are short polypeptide sequences (e.g., 88, 89, or 93 amino acid residues in length) that are nearly identical in structure. A nucleic acid sequence encoding a human SDF-1 polypeptide can be found in FIG. 10 and Gen-Bank® Accession No. NM_199168. A nucleic acid sequence encoding a mouse SDF-1 polypeptide can be found in FIGS. 11 and 12 as well as GenBank® Accession Nos. NM_021704 and NM_013655. Typically, an SDF-1 polypeptide is produced in cells as a precursor polypeptide that is inactive. The precursor can be cleaved to remove the amino-terminal sequence shown in bold, thereby revealing an active molecule. The portion of SDF-1 that interacts with its receptor, CXCR4, is underlined. This portion of SDF-1 is identical in the human and both mouse forms.

Human SDF-1 Polypeptide Sequence:

(SEQ ID NO: 4)

MNAKVVVVLVLVLTALCLSDGKP <u>V</u>SLSYRCPCRFFESHVARANVKHL

KILNTPCALQIVARLKNNNRQVCIDPKLKWIQEYLEKALN

Mouse SDF-1 Polypeptide Sequence, Alpha Form:

(SEQ ID NO: 5)

MDAKVVAVLALVLAALCISDGKP VSLSYRCPCRFFESHIARANVKHLK

ILNTPNCALQIVARLKNNNRQVCIDPKLKWIQEYLEKALNK

Mouse SDF-1 Polypeptide Sequence, Beta Form:

(SEQ ID NO: 6)

MDAKVVAVLALVLAALCISDGKP VSLSYRCPCRFFESHIARANVKHLK

ILNTPNCALQIVARLKNNNRQVCIDPKLKWIQEYLEKALNKRLKM

Elastase can cleave an SDF-1 polypeptide in vivo and in vitro within the CXCR4 interaction domain (underlined sequence). Cleavage by elastase can inactivate the biological activity of a SDF-1 polypeptide and occurs following the amino acid valine (enlarged and italic).

The following can be performed to generate and identify SDF-1 polypeptides have a particular activity (e.g., resistance to elastase cleavage). Briefly, the DNA encoding an SDF-1 polypeptide (e.g., murine SDF-1 alpha) can be cloned into an expression vector (e.g., the bacterial expression vector pET30). Using this vector, large quantities of SDF-1 polypeptides can be expressed and purified. In some cases, site-directed mutagenesis protocols can be used to alter the DNA sequence such that SDF-1 polypeptides having an altered primary amino acid sequence are produced. For example, SDF-1 polypeptides can be produced where the native amino acid sequence contains one or more mutations (e.g., additions, deletions, or substitutions). In some embodiments, the amino acid sequence of an SDF-1 polypeptide can be altered to enhance the resulting polypeptide's affinity for heparan sulfate. In addition, the amino acid sequence within the CXCR4 interacting domain of an SDF-1 polypeptide can be altered such that the resulting polypeptide can retain the ability to bind a CXCR4 polypeptide and reduce the responsiveness of a TLR4 polypeptide, while not losing the ability to activate a CXCR4 polypeptide. Any method can be used to express and evaluate an altered SDF-1 polypeptide for a particular biological property (e.g., resistance to elastase cleavage).

In one embodiment, an SDF-1 polypeptide can be designed such that is lacks the valine residue within its CXCR4 interaction domain. For example, this valine residue can be replaced with a leucine or isoleucine residue. In some cases, the SDF-1 polypeptide can be designed to have one of the following CXCR4 interaction domains: KPLSLSYR (SEQ ID NO:7); KPISLSYR (SEQ ID NO:8); KLVSLSYR (SEQ ID NO:9); KIVSLSYR (SEQ ID NO:10); KLISLSYR (SEQ ID NO:11); or KILSLSYR (SEQ ID NO:12). To increase an SDF-1 polypeptide's ability to bind heparan sulfate, the polypeptide can be designed to contain an RKRRAARR (SEQ ID NO:13) sequence or similar sequence (see., e.g., Cardin and Weintraub, *Arteriosclerosis* 9:21-32 (1989)). This sequence can be inserted anywhere along an SDF-1 polypeptide including, for example, before or after the CXCR4 interaction domain. For example, an SDF-1 polypeptide can be designed to contain an RKRRAARR sequence immediately following one of the following CXCR4 interaction domains: KPVSLSYR (SEQ ID NO:14), KPLSLSYR; KPISLSYR; KLVSLSYR; KIVSLSYR; KLISLSYR; or KILSLSYR.

Such SDF-1 polypeptide mutants as well as any potential CXCR4 binding agent can be tested to for the ability to bind a CXCR4 polypeptide, to activate a CXCR4 polypeptide, to reduce TLR4 responsiveness, and to be cleaved by a protease such as elastase.

The properties of an SDF-1 polypeptide, an altered SDF-1 polypeptide, or any potential CXCR4 binding agent can be tested in a series of cellular assays. For example, the ability to bind to a CXCR4 polypeptide can be tested using radioligand binding assays and/or using cell-based ELISA assays. In these cases, binding to, for example, CXCR4-expressing cells can be detected or quantitated using radiolabeled molecules (e.g., radiolabeled SDF-1 polypeptides) or anti-SDF-1 antibodies. Unlabeled molecules (e.g., unlabeled SDF-1 polypeptides) or antibodies that disrupt the SDF-1-CXCR4 interaction can be used in control experiment to confirm specificity of SDF-1 binding to CXCR4.

Biological activity of an SDF-1 polypeptide, an altered SDF-1 polypeptide, or any potential CXCR4 binding agent can be tested using any method. For example, the ability of an altered SDF-1 polypeptide to activate a CXCR4 polypeptide can be determined by assaying activation of intracellular signaling pathways normally activated by the binding of a SDF-1 polypeptide to a CXCR4 polypeptide (e.g., the use of an immunoblot determination of Erk-1 activation using anti-phospho-Erk-1 antibodies). In another example, the ability of an altered SDF-1 polypeptide to stimulate monocyte chemotaxis can be tested using a standard transwell cellular migration system. In yet another example, the ability of an altered SDF-1 polypeptide to reduce TLR4 responsiveness can be tested in a cell-based TLR4-activation assay as described herein.

In some embodiments, a CXCR4 binding agent can be evaluated using an in vivo model such as a mouse model of a disease to which TLR4 signaling is a prominent or contributing factor. In these cases, the contribution of TLR4 can be confirmed by comparing results from mice that lack TLR4 function to those results from control mice that are wild-type for TLR4. The C57BL10/ScN mouse strain is an example of a strain that lacks TLR4 function as this strain of mouse does not express TLR4. A control strain for this mouse can be C57BL10/SnJ. The C3H/HeJ mouse strain is another example of a strain that lacks TLR4 function as this strain expresses mutated TLR4 that does not stimulate intracellular signals in response to TLR4 agonists. A control strain for this mouse can be C3H/SnJ.

The following can be uses as a model for systemic inflammatory response syndrome. TLR4 activators injected into wild type mice, but not TLR4 mutant mice, can induce a systemic inflammatory response syndrome or SIRS. The SIRS includes inflammatory cytokine release, hypotension, vascular leak, organ failure, and death. The SIRS can resemble SIRS observed in humans following severe trauma, pancreatitis and/or sepsis. A potential CXCR4 binding agent can be administered prior to and at various times following initiation of SIRS. After receiving the potential CXCR4 binding agent, the animals can be evaluated to determine whether or not the severity of a SIRS symptom was reduced.

Similar methods can be used to assess potential CXCR4 binding agent for the ability to reduce the severity of a sepsis symptom using a model for sepsis or for the ability to reduce the severity of an ischemia-reperfusion injury using a model for ischemia-reperfusion injury. For sepsis, polymicrobial sepsis can be induced in mice using the cecal ligation and puncture technique. Many of the signs of sepsis that are seen in humans can be induced in the mice including fever, cytokine release, hypotension, infiltration of inflammatory cells into the lungs and liver, organ failure, and death. Ischemia-reperfusion injury can be induced in a mouse using experimental organ transplant protocols and/or surgical vascular occlusion protocols as described elsewhere (Squadrito et al., *Laboratory Investigation*, 83(8):1097-104 (2003)).

In some embodiments, an agent or treatment capable of increasing or decreasing expression of an SDF-1 polypeptide can be used to increase or decrease the responsiveness of a Toll-like receptor to a Toll-like receptor agonist. For example, G-CSF or TGF-β can be used to reduce expression of an SDF-1 polypeptide (Petit et al., *Nature Immunology*, 3(7): 687-694 (2002) and Wright et al., *Blood*, 102(6):1978-84 (2003)). Alternatively, low oxygen tension, a transcription factor (e.g., the transcription factor HIF-1), or antagonists of G-CSF or TGF-β can be used to increase expression of an SDF-1 polypeptide (Ceradini et al., *Nature Medicine*, 10(8): 858-64 (2004).

In other embodiments, an agent or treatment capable of increasing or decreasing expression of a CXCR4 polypeptide can be used to increase or decrease the responsiveness of a Toll-like receptor to a Toll-like receptor agonist. For example, bradykinin, IL-1β, oxidized low density lipoprotein component lysophosphatidylcholine, or G-CSF can be used to increase expression of a CXCR4 polypeptide (Petit et al., *Nature Immunology*, 3(7):687-694 (2002); Eddleston et al., *J. Immunology*, 169:6445-6451 (2002); and Han et al., *J. Leukocyte Biology*, 76:195-202 (2004)).

The invention will be further described in the following examples, which do not limit the scope of the invention described in the claims.

EXAMPLES

Example 1

Signaling by TLR4

Signaling through TLR4 is thought to initiate innate and adaptive immune responses. Signaling of TLR4 is usually studied using isolated cells, which are activated by sub-nanomolar concentrations of LPS. In normal tissues, however, cells bearing TLR4 reside in microenvironments containing large amounts of endogenous substances that can stimulate the receptor. Several models were developed to study how TLR4 functions in such microenvironments. An in vitro model system was developed using the human cell line HEK 293. An in vivo model was developed using mice that have wild type TLR4 receptor genes and normal TLR4 receptors or mice that have mutant TLR4 receptor genes and have defective or absent TLR4 receptors. The latter can be called "TLR4-deficient" mice. The following description demonstrates that signaling through TLR4 can be strongly inhibited by intact extracellular matrix and that inhibition can be abrogated and endogenous agonist(s) liberated when the matrix is degraded. Thus, release from inhibition rather than direct stimulation by agonists such as LPS can be an early event by which TLR4 initiates immune responses.

Reagents and Antibodies

Ultrapure heparan sulfate from bovine kidneys and END-X endotoxin removal resin were obtained from Seikagaku (Falmouth, Mass.). LPS from *Escherichia coli* was obtained from Sigma Aldrich (St. Louis, Mo.). Pancreatic elastase was obtained from Calbiochem (La Jolla, Calif.). Anti-TLR4/MD2 antibody clone MTS510 was obtained from e-Bioscience (San Diego, Calif.). Fluorescein isothiocyanate (FITC)-conjugated goat anti-rat IgG was obtained from Southern Biotech (Birmingham, Ala.). Anti-phospho p38 mitogen activated protein kinase (MAPK), anti-p38 MAPK, and Horseradish peroxidase-conjugated anti-rabbit antibodies were obtained from Cell Signaling Technology (Beverly, Mass.). Rat anti-mouse CD86 was obtained from Pharmingen (San Diego, Calif.). All materials used in cell culture were certified endotoxin free, or were treated with endotoxin removal resin and tested by the *Limulus amebocyte* lysate assay gel clot method (Seikagaku, Falmouth Mass.) to assure absence of detectable endotoxin.

Plasmid Construction

Total RNA was isolated from the murine macrophage cell line RAW 264.7 (ATCC, Manassas, Va.). This RNA was used to generate cDNA using the 1$^{st}$ Strand cDNA Synthesis Kit (Roche, Indianapolis, Ind.) for RT-PCR (AMV) with oligo-dt primers (15mer) and the following reaction conditions: 25° C. for 10 minutes, 42° C. for 60 minutes, 99° C. for 5 minutes, and 4° C. for 5 minutes. The resulting pool of cDNA was used as a template to amplify TLR4, MD2, and CD14 coding sequences by PCR. Reactions were carried out using Expand High Fidelity polymerase (Roche) and the following conditions: 94° C. for 2 minutes followed by 25 cycles of 94° C. for 1 minute, 55° C. for 1 minute, 68° C. for 3 minutes, and finishing with 72° C. for 7 minutes. TLR4 was amplified using the primers: TLR4 Forward 5'-CGC GGA TCC AGG ATG ATG CCT CCC TGG CTC-3' (SEQ ID NO:15), and TLR4 Reverse 5'-GGC GGT ACC TCA GGT CCA AGT TGC CGT TTC-3' (SEQ ID NO:16). MD2 was amplified using MD2 Forward 5'-CCG GAA TTC ATC ATG TTG CC-3' (SEQ ID NO:17), and MD2 Reverse 5'-CCG GAA TTC CTA ATT GAC ATC ACG-3' (SEQ ID NO:18). CD14 was amplified using CD14 Forward 5'-CCG GAA TTC ACC ATG GAG CGT GTG CTT GGC-3' (SEQ ID NO:19), and CD14 Reverse 5'-CCG GAA TTC TTA AAC AAA GAG GCG ATC TCC TAG-3' (SEQ ID NO:20).

PCR products were digested with appropriate restriction enzymes and cloned into eukaryotic expression plasmids. TLR4 was cloned into pcDNA3.1 (Invitrogen, Carlsbad, Calif.). MD2 was cloned into pcDNA3.1/Hygro (Invitrogen). CD14 was cloned into pcDNA4/myc-His with zeocin resistance (Invitrogen). Cloned sequences were screened by restriction digests for correct orientation. Nucleotide sequences were determined using dideoxynucleotide reaction of Sanger and automated detection system (Mayo Clinic Molecular Biology Core Facility) and then compared to published sequences of the genes. A NFκB-firefly luciferase reporter plasmid was obtained from Dr. Carlos Paya (Paya et al., *Proc. Natl. Acad. Sci., USA*, 89:7826-7830 (1992)). A control Renilla-luciferase reporter plasmid contained the Renilla-luciferase coding sequence under the control of the TK promoter (pTK-Renilla, Promega, Madison, Wis.).

Model Extracellular Matrix Environment

Tissue culture plates were coated with extracellular matrix as follows. Porcine aortic endothelial cells were seeded into 6-well ($3\times10^5$ cells/well), 24-well ($5\times10^4$ cells/well) or 100 mm ($2\times10^6$ cells) fibronectin-coated tissue culture plates (BD Biosciences, San Jose, Calif.) in DMEM (Invitrogen) containing 10% fetal bovine serum supplemented with penicillin and streptomycin and 4% w/v of Dextran 40. The cell cultures were incubated at 37° C. in 5% $CO_2$ humidified atmosphere for seven days and were supplemented with 50 μg/mL of ascorbic acid on day three and day five. After 7 days, endothelial cells were washed once with phosphate buffered saline (PBS) and lysed by exposure to 0.5% w/v Triton X-100 and 20 mM NH$_4$OH in PBS (pH 7.4) at 37° C. for 20 minutes (Bonifacino, J. S. (1998) Chapter 10: Extracellular Matrix. In Current Protocols in Cell Biology (Bonifacino, J. S., ed), John Wiley, New York, N.Y.). The wells were then washed 4 times with PBS (pH 7.4) and inspected microscopically to ensure removal of the cells. The plates were used immediately or were stored in PBS (pH 7.4) with 50 μg/mL of gentamycin at 4° C.

Generation of Extracellular Matrix Fragments

Tissue culture plates (100 mm) coated with extracellular matrix were treated with 1.0 mL elastase (0.1 U/mL) in PBS. The plates were sealed and incubated at 37° C. for 6 hours. The extracellular matrix fragments released from the plate by elastase were harvested and boiled for 30 minutes. The total protein content was determined using bicinchoninic acid assay (Pierce, Rockford, Ill.). For some experiments, the harvested extracellular matrix fragments in PBS were adjusted to pH 6.0 using 0.1 N HCl and incubated with 0.5 μg recombinant human heparanase (see below) at 30° C. for 16 hours. The samples were readjusted to pH 7.5 and boiled for 30 minutes, and the total protein concentration was determined.

Cell Culture and Transfection

HEK 293 cells (American Type Culture Collection, Manassas, Va.) were maintained at 37° C. in 5% humidified CO$_2$ in DMEM containing 10% fetal bovine serum and penicillin and streptomycin. RAW 264.7 cells were maintained at 37° C. in 10% humidified CO$_2$ in DMEM containing 10% fetal bovine serum and penicillin and streptomycin.

HEK 293 cells were stably transfected with the TLR4 and MD2 or CD14 expression plasmids, each of which encode a component of a complete, functional TLR4 receptor complex (Akira and Takeda, *Nat. Rev. Immunol.*, 4:499-511 (2004)) using Superfect (Qiagen, Valencia, Calif.) following the manufacturer's instructions. TLR4- and MD2- or CD14-expressing HEK 293 cells were obtained by culturing the transfected cells with appropriate antibiotic selection medium and cloning by limiting dilution in the selection medium. HEK 293 cells expressing TLR4, MD2, and CD14 were generated by transfecting HEK 293 cells expressing TLR4 and MD2 with the CD14 expression plasmid and selecting clones using appropriate antibiotic containing medium. Cell lines expressing TLR4 and MD2 and/or CD14 were then maintained in DMEM supplemented with 10% fetal bovine serum and the appropriate selection antibiotics. Control cell lines were transfected with empty expression vectors and incubated in selection conditions as described above.

Recombinant Heparanase

Human heparanase cDNA was cloned as described elsewhere (Dempsey et al., *Glycobiology*, 10:467-475 (2000)). Recombinant heparanase was produced using a baculoviral expression system and purified by affinity chromatography using heparin-agarose (McKenzie et al., *Biochem. J.*, 373: 423-435 (2003)). The recombinant enzyme was dialyzed into PBS, pH 7.4, and concentrated to 57 μg/mL using Centricon 10,000 MWCO centrifugal concentrators, sterilized by filtration using 0.2 μm filters, and stored at −70° C. until used.

Radiolabeling and Depolymerization of Heparan Sulfate

[$^3$H]heparan sulfate was prepared by reducing heparan sulfate using [$^3$H]BH$_4$ (Amersham) as described elsewhere (Ihrcke et al., *J. Cell. Physiol.*, 175:255-267 (1998)). The radiolabeled product had a specific activity of 15 mCi/g. Heparan sulfate or [$^3$H]heparan sulfate (20 mg/mL in water) were depolymerized by deaminative cleavage with nitrous acid (Conrad, H. E. (2001) Degradation of heparan sulfate by nitrous acid. In Methods in Molecular Biology (Iozzo, R. V., ed) Vol. 171 pp. 347-351, Humana Press, Totowa, N.J.) and then neutralized. To monitor cleavage reactions, fragments of [$^3$H]heparan sulfate were separated using 10DG gel filtration columns (Biorad, Hercules, Calif.). Eluted fractions (0.25 mL) were collected, and the [$^3$H]heparan sulfate was detected by scintillation counting. Two types of depolymerization by nitrous acid were performed. Nitrous acid used at pH 1.5 cleaves heparan sulfate completely (at sulfated glucosamine residues) generating small fragments that eluted in late fractions from the column. Nitrous acid at pH 4.0 cleaves heparan sulfate at unmodified glucosamine residues, which are infrequent in the heparan sulfate molecule and therefore generate large fragments that elute in early fractions from the column.

In some experiments, heparan sulfate was depolymerized with recombinant human heparanase as follows. Four micrograms of [$^3$H]heparan sulfate was incubated with 0.5 μg of recombinant human heparanase at 30° C. in 0.1M sodium acetate, 0.1% bovine serum albumin buffer, pH 6.5. After 16 hours, the reaction was stopped by increasing the pH to 8.0 and boiling for 30 minutes. The reactions were loaded onto Hi-Trap Q columns (Amersham-Pharmacia, Piscataway, N.J.), and the heparan sulfate fragments were eluted with a linear gradient of NaCl (0 to 1M). Radioactivity in the eluted fractions (0.5 mL) was detected by scintillation counting. Since heparanase cleaves heparan sulfate adjacent to sulfated domains (Okada et al., *J. Biol. Chem.*, 277:42488-42495 (2002)) disrupting the charge density on the molecule, the cleaved product eluted from columns in earlier fractions compared to control heparan sulfate.

NFκB-Luciferase Reporter Assays

Activation of NFκB was measured using a NFκB-luciferase reporter assay. HEK 293 cell lines stably expressing TLR4, MD2, and/or CD14, or control cells were seeded into 24 well tissue culture plates (2×10$^5$ cells/well) in 1.0 mL DMEM containing 10% fetal bovine serum and penicillin and streptomycin. The cells were allowed to adhere to the culture wells at 37° C. overnight and were then transfected with 0.1 μg pTK Renilla-luciferase and 0.1 μg NFκB-firefly-luciferase using Superfect Transfection Reagent (Qiagen). Following transfection, the cells were washed once with phosphate buffered saline and cultured for 24 hours at 37° C. in 1.0 mL DMEM containing 0.5% fetal bovine serum. After various treatments, the culture medium was aspirated, and the cells were washed once with PBS. The cells were then lysed in 150 μL Passive Lysis Buffer (Promega) with rocking at room temperature for 15 minutes. Renilla- and Firefly-luciferase were assayed simultaneously using Dual-Luciferase Reporter Assay System (Promega) and a TD-20/20 luminometer (Turner Designs, Sunnyvale, Calif.). Activation of NFκB was reported as a ratio of the firefly luciferase activity to the constitutively expressed Renilla luciferase internal control, and as the mean of triplicate wells.

Animals

TLR4-deficient C57BL/10ScN mice, which have a deletion in chromosome 4 that encompasses the TLR4 gene, were obtained from The National Cancer Institute (Bethesda, Md.). C57BL/10SnJ mice, which have wild type TLR4 and are congenic with C57BL/10ScN were obtained from the Jackson Laboratory (Bar Harbor, Me.).

Surgical Procedures and Immunohistochemistry

Mice were anesthetized, and the spleen was directly visualized through an incision in the lateral abdominal wall. TLR4 activators dissolved in 50 μL of PBS were injected into the spleen as follows. The solutions were injected as a 27 gauge needle was withdrawn along the long axis of the organ. Twelve hours after injection, the spleens were harvested and frozen in liquid nitrogen for analysis of CD86 expression. Studies were performed at twelve hours because preliminary experiments indicated CD86 expression became clearly detectable at this time. Longitudinal tissue sections were prepared from the center of the spleen and stained as described elsewhere (Dempsey et al., *Glycobiology*, 10:467-475 (2000)) with the following modifications. Secondary detection antibodies were diluted in M.O.M. diluent (Vector Laboratories, Burlingame, Calif.) and preabsorbed with mouse serum (Jackson ImmunoResearch Laboratories, West Grove, Pa.). Fluorescent images were converted to grayscale using SPOT software (Diagnostic Instruments, Sterling Heights, Mich.).

Results

Extracellular Matrix Conditions TLR4 Signaling

To determine how cells expressing the TLR4 receptor complex (Akira and Takeda, *Nat. Rev. Immunol.*, 4:499-511 (2004)) function in microenvironments rich in endogenous agonists, a model system was developed that would allow one to measure TLR4 activation in cells exposed to extracellular matrix rich in endogenous agonists such as heparan sulfate (Platt et al., *J. Exp. Med.*, 171:1363-1368 (1990) and Ihrcke and Platt, *J. Cell. Physiol.*, 168:625-637 (1996)). HEK 293 cells were stably transfected with components of the TLR4 complex (HEK/TLR4(+) cells). Since heparan sulfate and LPS both stimulate NFκB activity via TLR4, the HEK/TLR4 (+) cells were transiently transfected with a NFκB-luciferase reporter gene to monitor TLR4 activation. The cells responded both to LPS and heparan sulfate (FIG. 1). When the HEK/TLR4(+) cells were cultured on plates coated with extracellular matrix that is rich in heparan sulfate proteoglycans, the cells exhibited a low baseline level of NFκB-luciferase activity similar to HEK/TLR4(+) cells cultured in plates coated with fibronectin (which does not stimulate TLR4) (FIG. 2A). In striking contrast to cells exposed only to fibronectin, HEK/TLR4(+) cells cultured on extracellular matrix responded minimally to stimulation with heparan sulfate (FIG. 2A) or with LPS (FIG. 2B). Expression of TLR4/MD2 was not different in cells cultured on extracellular matrix or fibronectin (FIG. 2C). Inhibition of TLR4 by extracellular matrix was not unique to HEK/TLR4(+) cells nor to NFκB activation, as RAW 264.7 macrophages, which naturally express TLR4 complexes, exhibit blunted activation of p38 MAP kinase in response to heparan sulfate or LPS when cultured in extracellular matrix (FIGS. 2D and E). In the absence of extracellular matrix, p38 MAP kinase was fully activated, as previously shown (Johnson et al., *J. Immunol.*, 168:5233-5239 (2002)).

Figure 2:
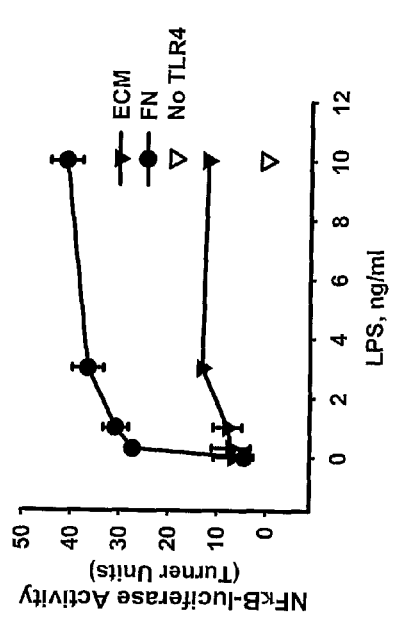
FIG. 2. TLR4 signaling is conditioned by extracellular matrix. The impact of extracellular matrix on TLR4 activation was tested in cells cultured in wells coated with extracellular matrix. (A) and (B) Inhibition of NFκB activation by extracellular matrix in HEK/TLR4(+) cells. HEK/TLR4(+) cells were cultured in wells coated with extracellular matrix (ECM) or fibronectin (FN) and transfected with NFκB- and control-luciferase reporter genes. TLR4 signaling in response to increasing amounts of heparan sulfate (A) or LPS (B) was measured six hours after stimulation. (C) Effect of extracellular matrix on cell surface expression of TLR4/MD2. HEK/TLR4(+) cells were cultured in wells coated with fibronectin (FN) or fibronectin plus extracellular matrix (ECM). The cells were tested for cell surface expression of the TLR4/MD2 complex by flow cytometry using monoclonal antibodies specific for that complex. As a control, HEK cells that do not express TLR4 were tested using the same monoclonal antibody (No TLR4). TLR4/MD2 expression did not differ in cells cultured in wells coated extracellular matrix from those cultured in wells coated with fibronectin. (D) and (E) Inhibition of p38 MAP Kinase activation by extracellular matrix in RAW 264 cells. (D) RAW 264.7 murine macrophages were cultured in wells coated with extracellular matrix (ECM) or fibronectin (FN). The cells were stimulated with heparan sulfate (left panel) or LPS (right panel) for the indicated time (minutes), after which the cells were lysed and activated p38 MAPK (phospho p38) was measured by immunoblotting. (E) Densitometry scanning of immunoblot films from (C) indicates that activation of p38 phosphorylation, relative to total p38, was 60% lower in cells cultured in the presence of ECM and stimulated with heparan sulfate. Similar results were obtained for cells stimulated with LPS. The data shown are representative of 3 separate experiments and indicate that activation of TLR4 signaling is inhibited by extracellular matrix.
Figure 2:
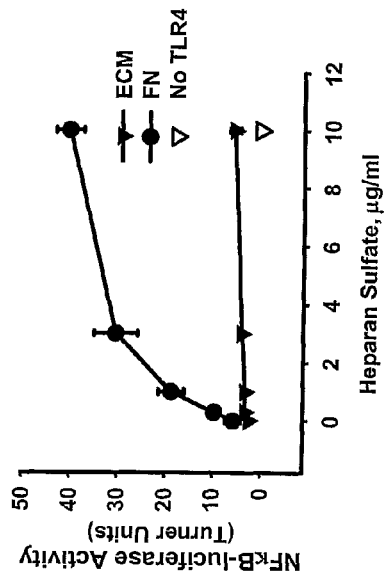
Figure 2:
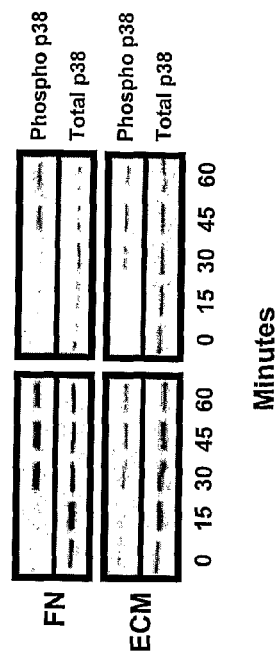
Figure 2:
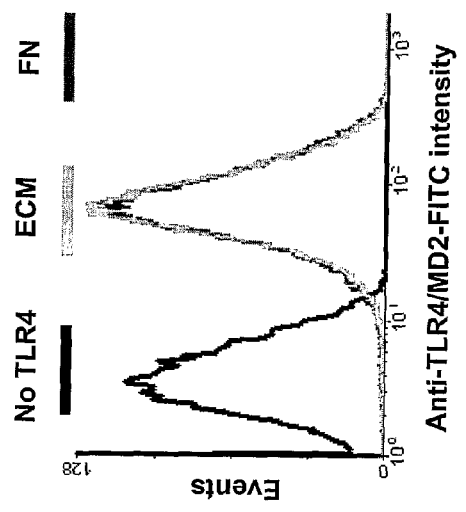
Figure 2:
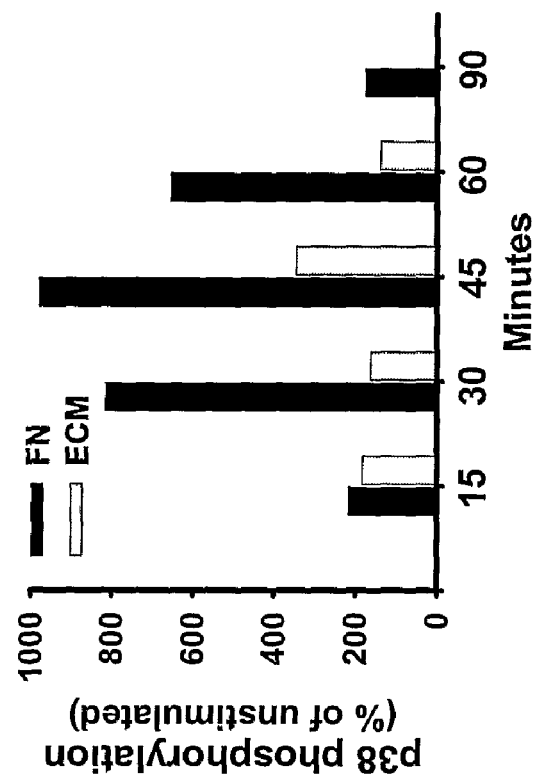
Figure 3:
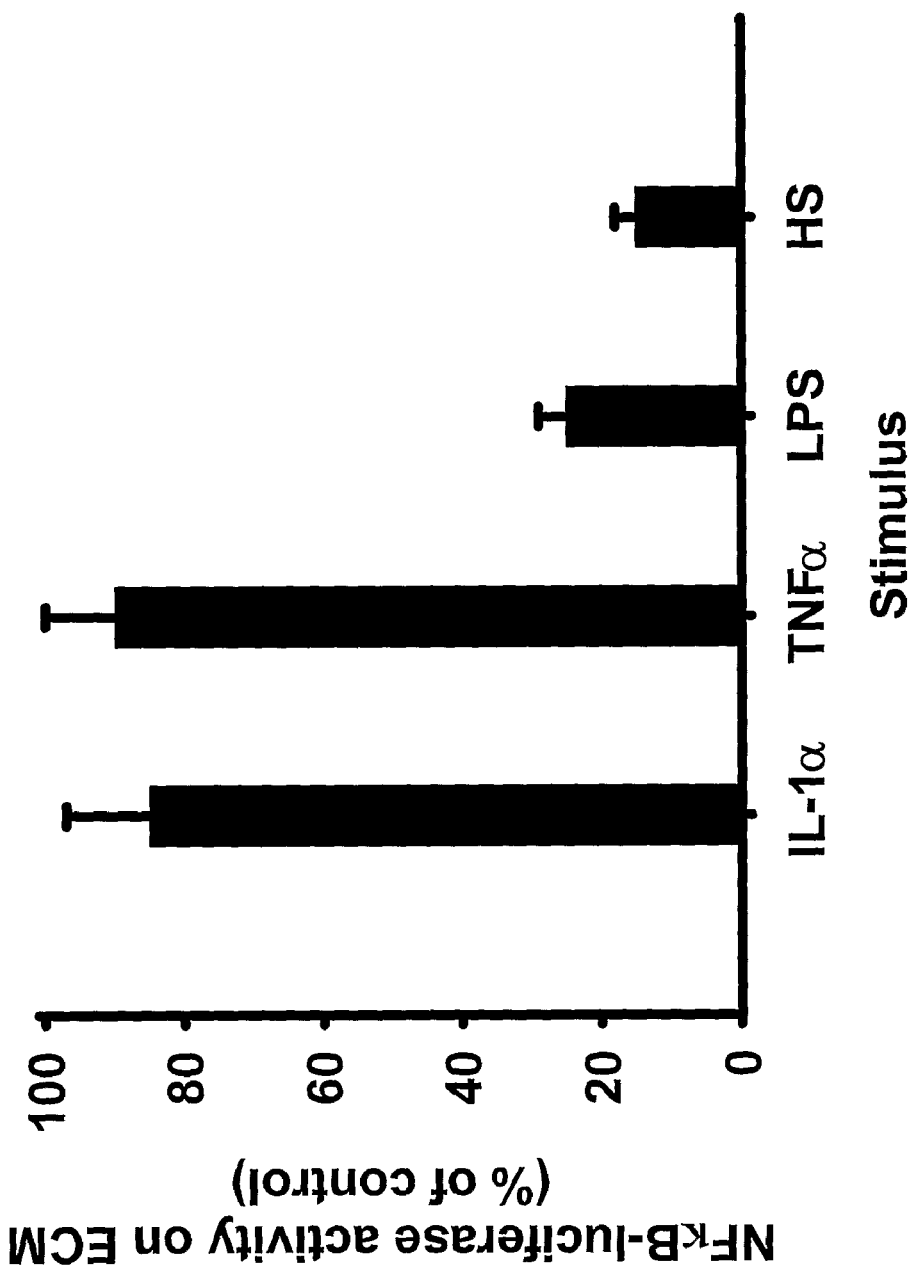
FIG. 3. Extracellular matrix specifically conditions TLR4 activation. To determine whether extracellular matrix inhibits TLR4 complexes or components of the intracellular signaling apparatus, the impact of extracellular matrix on other activators of NFκB signaling was tested. HEK/TLR4(+) cells were cultured in wells coated with extracellular matrix or wells coated with fibronectin and transfected with NFκB- and control-luciferase reporter plasmids. The transfected cells were treated with 10 ng/mL of recombinant human IL-1α or TNFα for 6 hours. NFκB-luciferase activity from cells grown in extracellular matrix-coated wells is expressed as a percentage of the activity from cells grown in control fibronectin-coated wells. Results from HEK/TLR4(+) cells stimulated with heparan sulfate (HS) or LPS are shown for comparison. These results indicate that extracellular matrix specifically inhibits TLR4 signaling and suggests the inhibition is exerted on the TLR4 complexes and not on common intracellular signaling intermediates.

The following experiment was performed to test whether suppression of TLR4 signaling by extracellular matrix is at the level of TLR4 complexes or the intracellular signaling apparatus. To address this question, activation of NFκB signaling by IL-1α and TNFα, cytokines that use the same intracellular components as TLR4 was measured (Magor and Magor, *Dev. Comp. Immunol.*, 25:651-682 (2001)). Although the absolute degree of signaling in response to IL-1α or TNFα varied, the NFκB signal was approximately 10% lower in cells cultured in extracellular matrix compared to cells cultured on fibronectin (FIG. 3). This lower level of NFκB signaling contrasts with the 80%-90% decrease observed when TLR4 agonists (LPS or heparan sulfate) were used (FIGS. 2 and 3). These results indicate that extracellular matrix acts on TLR4 complexes and minimally or not at all on the intracellular signaling apparatus.

Figure 4:
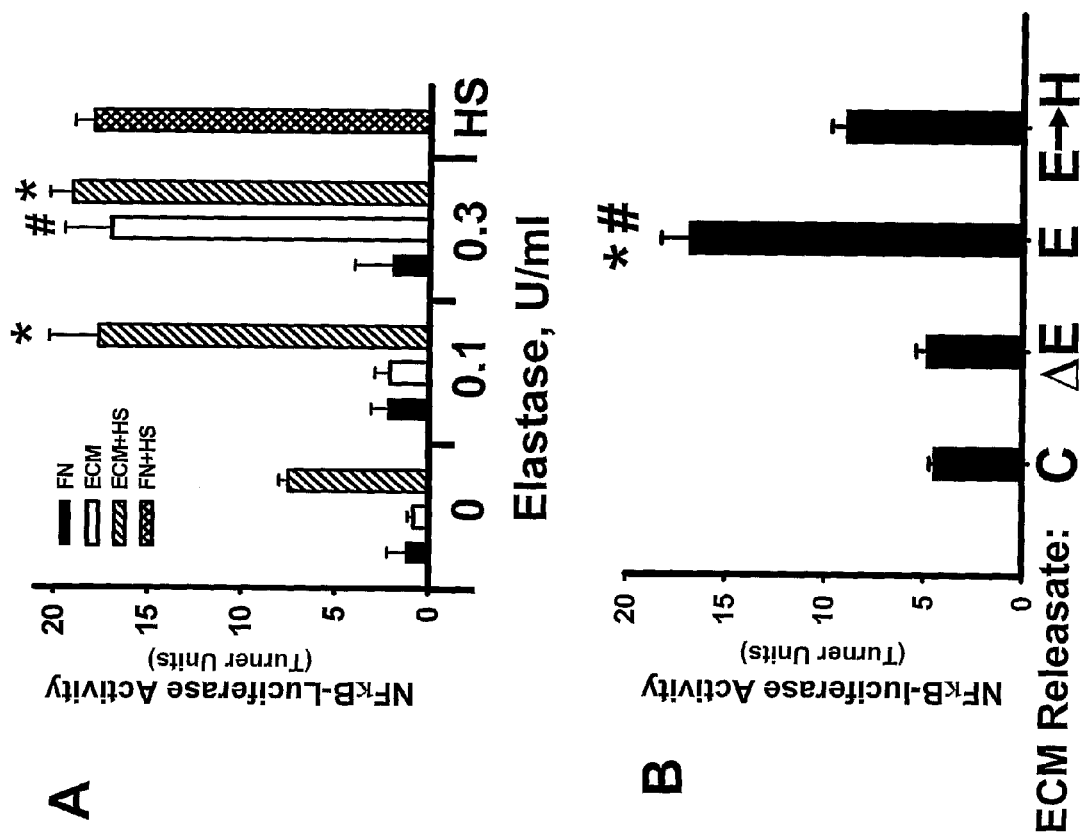
FIG. 4. Conditional inhibition of TLR4 signaling is released by elastase. (A) To determine if degradation of extracellular matrix by elastase would release TLR4 from inhibition, HEK/TLR4(+) cells were cultured in wells coated with extracellular matrix (ECM) or fibronectin (FN) and transfected with NFκB- and control-luciferase reporter plasmids. The cells were treated for 4 hours with elastase with or without 1 µg/mL of heparan sulfate (HS). Treatment with elastase at 0.1 U/mL increased TLR4 responses to heparan sulfate by about 3 fold compared to treatment with heparan sulfate in the absence of elastase (*p<0.05). Treatment with elastase at 0.3 U/mL stimulated full TLR4 responses without addition of agonist (#p<0.05). Cells grown on fibronectin did not respond to elastase but responded fully to HS. (B) Heparan sulfate in extracellular matrix activates TLR4. The contribution of heparan sulfate to the ability of material released from extracellular matrix (ECM) by elastase (E) to stimulate TLR4 was tested. Controls included material released during incubation with heat inactivated elastase (ΔE) or the PBS vehicle (C). A fraction of extracellular matrix fragments generated by elastase was incubated with recombinant heparanase prior to stimulating HEK/TLR4(+) cells (E→H). The results show that heparanase destroys most of the agonist activity of ECM releasate. *p<0.05 compared to control, #p<0.05 compared to (E→H).

If extracellular matrix inhibits TLR4 activation, then one question is how that inhibition is relieved so that immunity and resistance to infection can be mounted. Whereas signaling through TLR4 is constitutively constrained in unperturbed tissues, constraint might be relieved if extracellular matrix is cleaved by proteases (Kainulainen et al., *J. Biol. Chem.*, 273:11563-11569 (1998) and Saadi et al., *FASEB J.*, 16:849-856 (2002)). To test this possibility, the following experiment was performed to determine whether elastase, a protease released by neutrophils, relieves inhibition of TLR4 complexes conferred by extracellular matrix. Consistent with that concept, HEK/TLR4(+) cells in extracellular matrix responded vigorously to heparan sulfate if the cells were treated with low concentrations (0.1 U/mL) of elastase (FIG. 4A). Elastase by itself did not stimulate HEK/TLR4(+) cells (FIG. 4A), but HEK/TLR4(+) cells on extracellular matrix treated with a higher concentration of elastase (0.3 U/mL) responded even without added heparan sulfate. Thus, digestion of extracellular matrix relieves constraint on TLR4 activation and generates endogenous agonists for the receptor. While various components of extracellular matrix might suppress TLR4 function, at least some suppression may be caused by the presence of heparan sulfate in the matrix. Matrix produced by Hela cells was found to suppress TLR4 signaling. In addition, the level of suppression was found to be reduced by two thirds if the Hela cells were stably transfected with human heparanase. Thus, the same substance, heparan sulfate, that can serve as an agonist of TLR4, can, as part of undisturbed matrix, contribute to suppression of signaling by TLR4.

Cleaved Components of Extracellular Matrix Activate TLR4 Signaling

The following experiments were performed to determine whether the endogenous TLR4 agonist generated by elastase is heparan sulfate. Specifically, experiments were performed to test whether constituents of extracellular matrix liberated by elastase activate HEK/TLR4(+) cells and whether activation is abolished by selective digestion of heparan sulfate. As shown in FIG. 4B, fragments of extracellular matrix released by elastase activated HEK/TLR4(+) cells to the same extent as direct treatment of the cells on extracellular matrix with elastase or treatment of control cells with a TLR4 agonist. Incubation of extracellular matrix releasate with heparanase decreased the heparan sulfate content by 50% and the ability of the releasate to activate HEK/TLR4(+) cells by 50% (FIG. 4B). This percentage decrease is equivalent to the decrease in agonist activity of purified heparan sulfate incubated with purified heparanase (FIG. 1C). These results demonstrate that heparan sulfate is the major agonist generated when elastase acts on extracellular matrix.

Extracellular Matrix Cleaved In Vivo Activates TLR4

Figure 5:
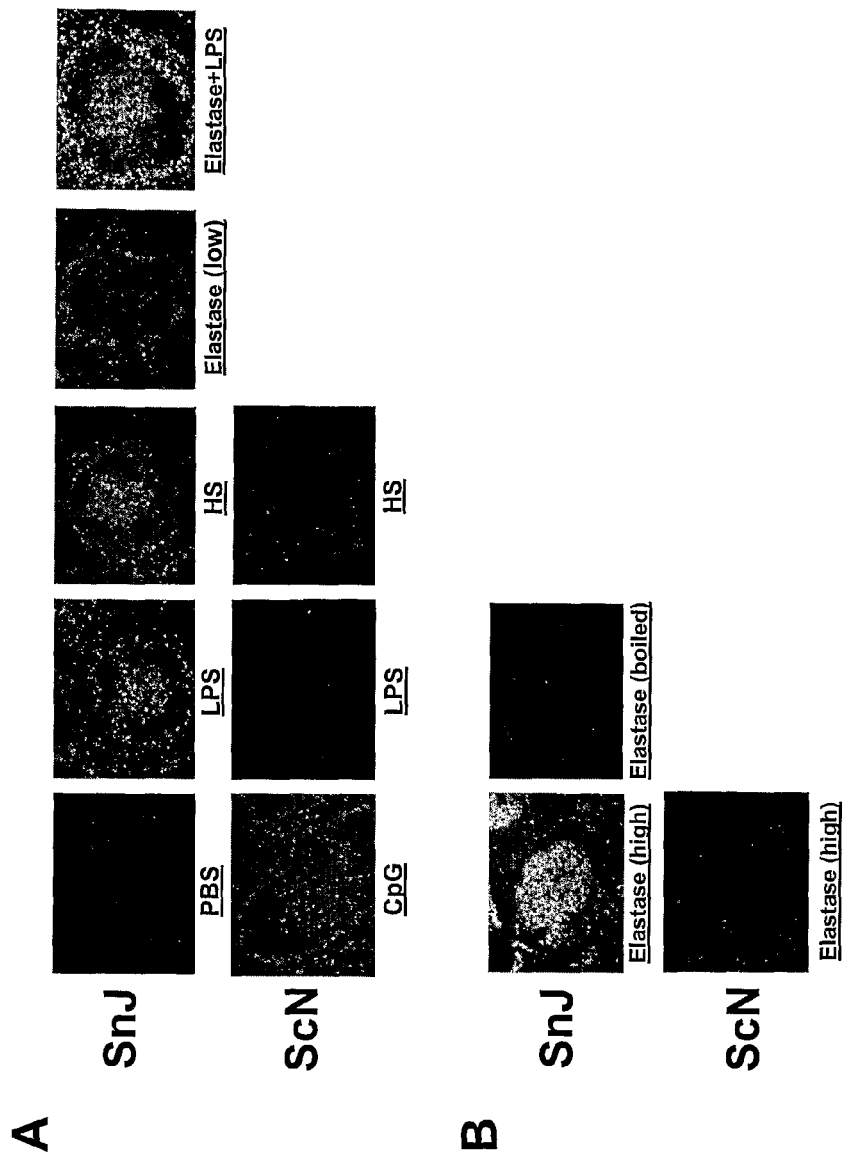
FIG. 5. Elastase relieves constraint on TLR4 signaling in vivo. Whether TLR4 signaling is constitutively constrained and whether elastase releases that constraint in vivo was tested. Spleens of wild type mice and mice lacking TLR4 function were injected with heparan sulfate (HS) or with LPS with or without a small amount of elastase to relieve constraint on TLR4 signaling. Alternatively, a higher amount of elastase was injected alone to generate endogenous TLR4 activator(s). Expression of CD86 was assayed in the spleen by immunopathology twelve hours after administration of elastase. (A) Spleens of C57BL/10SnJ mice with wild-type TLR4 (SnJ) were injected with 10 ng LPS, 10 µg of heparan sulfate (HS), 0.01 U elastase (Elastase (low)), or 0.01 U elastase+1 ng LPS (Elastase+LPS). Spleens of control C57BL/10 ScN mice that lack TLR4 function (ScN) were injected with 10 ng LPS, 10 µg of heparan sulfate (HS) or 300 ng CpG DNA. Control mice were injected with the vehicle alone, 50 µL of PBS. (B) Spleens of mice with wild-type TLR4 (SnJ) or that lack TLR4 function (ScN) were injected with 0.1 U of elastase (Elastase (high)) or inactive elastase (elastase (boiled)). Spleens from normal (SnJ) mice had modestly increased expression of CD86 in response to heparan sulfate, LPS or low dose elastase, however low dose elastase enhanced expression of CD86 in response to LPS. Higher dose elastase (0.1 U) induced profound expression of CD86. Expression of CD86 was absent in spleens from mice that lack TLR4 (ScN), which responded only to the TLR9 activator CpG DNA. The results demonstrate that extracellular matrix limits TLR4 signaling in response to LPS and that cleavage of extracellular matrix both facilitates TLR4 responses to exogenous activators and triggers TLR4 responses by generating endogenous activators in vivo.

To test whether elastase activates TLR4 responses in living tissues, the properties of cells in the spleens of mice injected with TLR4 activators with or without elastase were studied. Injection of 10 ng of LPS or small amounts (0.01 U) of elastase only modestly increased expression of CD86, a protein expressed in response to TLR4 signaling (Kaisho and Akira, *Biochim. Biophys. Acta*, 1589:1-13 (2002)), in splenocytes in intact spleens (FIG. 5). Similar increases in CD86 were observed in spleens injected with 10 μg of heparan sulfate (FIG. 5). Injection of a smaller amount of LPS (1 ng) did not increase expression of CD86, but injection of 1 ng LPS along with a small amount of elastase, or injection of increased amounts (0.1 U) of elastase alone, profoundly increased expression of CD86 (FIG. 5). These changes in CD86 expression induced by elastase required TLR4 function, as the increases in CD86 were not observed when elastase or LPS were injected into spleens of mice which lack TLR4 function (FIG. 5). These results demonstrate that extracellular matrix limits TLR4 signaling in response to exogenous activators in intact tissues, and that cleavage of extracellular matrix facilitates TLR4 responses to exogenous agonists and also triggers TLR4 signaling by generating endogenous agonists.

The results presented herein raise the question of how heparan sulfate in intact extracellular matrix inhibits TLR4 if the same molecule in soluble form stimulates TLR4. The extracellular matrix of cells expressing recombinant heparanase suppresses TLR4 signaling far less than normal matrix. This raises the possibility that heparan sulfate in extracellular matrix either directly or through attachment to other molecules interacts with TLR4, suppressing signal transduction. Consistent with this possibility, SDF-1, which is tethered by heparan sulfate, was found to suppress TLR4 signaling as described herein.

Constraint of TLR4 signaling may help avert unwanted activation of innate immunity. On the other hand, the release of proteases, as it occurs in infection or tissue injury, degrades extracellular matrix relieving constraint on TLR4 function, and allowing small amounts of agonists to stimulate the receptor. If sufficient degradation of matrix occurs, endogenous agonists, particularly heparan sulfate, can stimulate TLR4. Of course, very large amounts of LPS or other agonists might bypass this suppressive mechanism or might induce the sepsis syndrome by acting on cells in blood vessels that are not embedded in matrix. However, the results provided herein suggest that in normal tissues, the first step in the genesis of innate and adaptive immunity is not necessarily the stimulation of TLR4 as previously thought (Medzhitov and Janeway, *Science*, 296:298-300 (2002)), but rather the release of TLR4 from constitutive inhibition by extracellular matrix. Since nearly every type of tissue injury, infection, or inflammation causes degradation of heparan sulfate proteoglycans, the TLR4-heparan sulfate interaction is uniquely poised to monitor threats to well being from exogenous or endogenous origin.

The results provided herein also help explain how the sepsis syndrome and SIRS arise. The sepsis syndrome is thought to be triggered by LPS released from infecting bacteria, and can be reproduced in animals by administration of large amounts of LPS (Galanos et al., *Proc. Natl. Acad. Sci. USA*, 76:5939-5943 (1979)). While activation of TLR4 by LPS may certainly precipitate the sepsis syndrome, human subjects with this condition often do not have detectable bacteria or LPS in the blood. In fact, SIRS is defined as a sepsis-like condition, observed in severe trauma, pancreatitis, and cancer, occurring in the absence of detectable infection (Paterson and Webster, *J. R. Coll. Surg. Edinb.*, 45:178-182 (2000)). Common to the sepsis syndrome and to SIRS is the release of proteases. Elastase, which is released from activated neutrophils and inflamed pancreatic cells, or matrix metalloproteases released from activated endothelium might well relieve constraints on TLR4, allowing it to be stimulated by endogenous agonists, including those released by the proteases. Elastase can precipitate a TLR4-dependant SIRS in mice (Johnson et al., *J. Immunol.*, 172:20-24 (2004)), and the protease activity of elastase on extracellular matrix can generates endogenous activators of TLR4. Involvement of endogenous activators of TLR4 may also explain why LPS antagonists have failed to be of benefit in treatment of sepsis (Dunn, *Surg. Infect.* (Larchmt), 1:227-237 (2000)). The data provided herein demonstrate that therapeutic measures aimed at blocking elastase or matrix metalloproteases can control TLR4 function and reduce the production of endogenous TLR4 activators.

Example 2

Reducing TLR4 Activation

TLR4 exists and functions as a receptor complex which in addition to TLR4 includes MD2 and CD14. Other cell surface polypeptides, including heat shock protein (HSP) 70 and HSP90, growth and differentiation factor 5 and chemokine receptor 4 (CXCR4), can participate in TLR4 signaling (Triantafilou et al, *J. Cell Sci.*, 115:2603-2611 (2002) and Triantafilou and Triantafilou, *Trends Immunol.*, 23:301-304 (2002)). How these proteins function as a putative "LPS activation cluster" is not known. The following demonstrates that CXCR4 can modulate the ability of TLR4 to be activated.

Experimental Procedures

Sources of Reagents and Antibodies

LPS from *Escherichia coli* was obtained from Sigma-Aldrich (St. Louis, Mo.). A neutralizing monoclonal antibody specific for chemokine receptor 4 was obtained from R&D Systems Inc. (Minneapolis, Minn.). Monoclonal anti-CXCR4 and control mouse IgG2a κ conjugated to allophycocyanin (APC) were obtained from BD Biosciences (San Diego, Calif.). Fluorescein isothiocyanate (FITC)-conjugated antibodies were obtained from Southern Biotechnology Association (Birmanhgam, Ala.). Anti-Mouse TLR4/MD-2 was obtained from BioSource (Camarillo, Calif.). Pertussis Toxin (*Bordatella Pertussis*) and Pertussis Toxin-B (apoenzyme) were obtained from CalBiochem (La Jolla, Calif.). All materials used in cell culture were certified endotoxin free or were treated with endotoxin removal resin and tested by the *Limulus amebocyte* lysate assay gel clot method (Seikagaku, Falmouth, Mass.) to assure absence of detectable endotoxin.

Plasmid Construction

Expression vectors encoding components of the TLR4 complex were prepared as follows. Total RNA isolated from the murine macrophage cell line RAW 264.7 (American Type Culture Collection, Manassas, Va.) was used to generate cDNA using the "$1^{st}$ Strand cDNA Synthesis Kit" (Roche, Indianapolis, Ind.) for RT-PCR (AMV) with oligo-dt primers, according to the manufacturer's recommended protocol. The resulting pool of cDNA was used as a template in PCR to amplify sequences encoding TLR4, MD2, and CD14, using "Expand High Fidelity" polymerase (Roche). TLR4 was amplified using the primers: TLR4 Forward 5'-CGC GGA TCC AGG ATG ATG CCT CCC TGG CTC-3' (SEQ ID NO:15), and TLR4 Reverse 5'-GGC GGT ACC TCA GGT CCA AGT TGC CGT TTC-3' (SEQ ID NO:16). MD2 was amplified using MD2 Forward 5'-CCG GAA TTC ATC ATG TTG CC-3' (SEQ ID NO:17), and MD2 Reverse 5'-CCG GAA TTC CTA ATT GAC ATC ACG-3' (SEQ ID NO:18). CD14 was amplified using CD14 Forward 5'-CCG GAA TTC ACC ATG GAG CGT GTG CTT GGC-3' (SEQ ID NO:19), and CD14 Reverse 5'-CCG GAA TTC TTA AAC AAA GAG GCG ATC TCC TAG-3' (SEQ ID NO:20).

PCR products were cloned into eukaryotic expression plasmids (Invitrogen, Carlsbad, Calif.): TLR4 into pcDNA3.1, MD2 into pcDNA3.1/Hygro, and CD14 into pcDNA4/myc-His with zeocin resistance. Cloned sequences were screened for correct orientation and sequence. A NFκB-firefly luciferase reporter plasmid was obtained from Dr. Carlos Paya (Mayo College of Medicine, Rochester, Minn.). Control Renilla-luciferase reporter plasmid was pTK-Renilla (Promega, Madison, Wis.). The YFP-CXCR4 expression plasmid was prepared by cloning the CXCR4 coding sequence (Orsini et al., *J. Biol. Chem.*, 274:31076-31086 (1999)) into the pEYFP-C1 vector (Clontech, Palo Alto, Calif.) with the vector encoded yellow fluorescent protein appended in frame with the carboxy-terminus of the CXCR4 coding sequence.

Cell Cultures

HEK 293 cells (human embryonic kidney cells) from American Type Culture Collection (ATCC) were cultured in DMEM containing 10% fetal bovine serum, penicillin, and streptomycin. HEK 293 cells were transfected with TLR4, MD2, and CD14 expression plasmids using the Superfect transfection reagent (Qiagen, Valencia, Calif.), as suggested by the manufacturer for stable transfection. TLR4/MD2/CD14 expressing HEK 293 cells were selected using appropriate antibiotic selection medium and were then cloned by limiting dilution in the same medium. Control cells were prepared using empty expression vectors and identical transfection and selection procedures.

Stimulation of HEK 293 Cells

HEK 293 cell lines stably expressing TLR4/MD2/CD14 were seeded into 24-well tissue culture plates ($2\times10^5$ cells/well) and allowed to adhere at 37° C. overnight. The adherent cells were transfected with 0.1 µg pTK Renilla-luciferase and 0.1 µg NFκB-firefly-luciferase using Superfect Transfection Reagent (Qiagen) and then cultured for 24 hours at 37° C. in 1 mL DMEM containing 0.5% fetal bovine serum. The cells were stimulated as indicated, washed with phosphate buffered saline, and lysed with 150 µL Passive Lysis Buffer (Promega). The amount of Renilla- and Firefly-luciferase in the cell lysates was assayed simultaneously using Dual-Luciferase Reporter Assay System (Promega) and a TD-20/20 lumenometer (Turner Designs, Sunnyvale, Calif.). Activation of NFκB-firefly luciferase reporter activity is given as the ratio of firefly luciferase to the internal control Renilla luciferase activity, determined and expressed as the mean of triplicate wells.

Flow Cytometry

Flow cytometric analysis was performed as described elsewhere (Kodaira et al., *J. Immunol.*, 165:1599-1604 (2000)). HEK 293 cells were incubated with APC-conjugated anti-CXCR4 monoclonal antibodies and analyzed by FACScan using CellQuest software (Becton Dickinson, San Jose, Calif.).

Results

CXCR4 and the TLR4 Response to LPS

Figure 6:
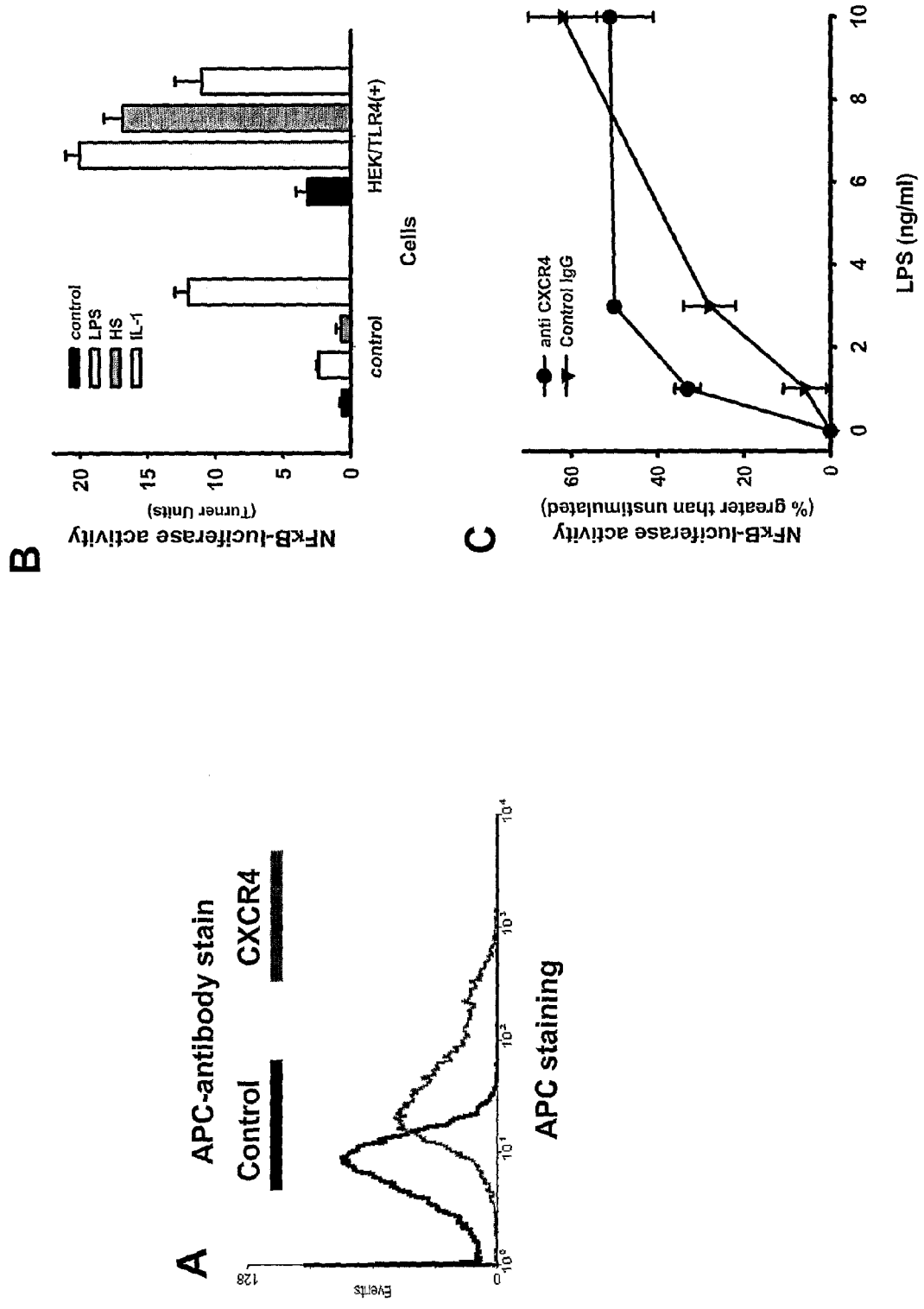
FIG. 6. Modulating TLR4 activity in HEK 293 cells. Whether CXCR4 modifies TLR4 activation was tested by measuring the impact of perturbing CXCR4 using monoclonal antibodies, and testing the effect of this treatment on TLR4 activation by LPS in HEK 293 cells. For this end, HEK 293 cells were stably transfected with murine TLR4, MD2, and CD14 expression plasmids, and cell lines that express these polypeptides were selected (HEK/TLR4(+) cells). The cells were then characterized and tested as shown in this figure. (A) CXCR4 expression on HEK/TLR4(+). CXCR4 expression on HEK/TLR4(+) cells was determined by flow cytometry using anti-CXCR4 or control APC-conjugated monoclonal antibodies. The results show that HEK/TLR4(+) cells express CXCR4. (B) Stimulation of HEK 293 cells by LPS and heparan sulfate. HEK/TLR4(+) cells or control HEK 293 cells (that lack TLR4) were transfected with NFκB-firefly luciferase and internal control Renilla-luciferase reporter plasmids and then tested for response to 10 ng/mL of LPS, 10 μg/mL of heparan sulfate, or 10 ng/mL recombinant human IL-1α. NFκB-activated luciferase expression was measured four hours after stimulation, results shown are the mean of triplicate wells. These results, which are representative of 3 experiments, show that HEK/TLR4(+) cells respond to LPS and heparan sulfate. (C) Impact of CXCR4 on activation of TLR4 by LPS. To determine if CXCR4 affects the ability of LPS to activate TLR4, HEK/TLR4(+) cells were transfected with NFκB- and control luciferase reporter plasmids and then treated with 25 μg/mL anti-CXCR4 monoclonal antibodies or control antibodies of the same isotype for thirty minutes, after which the indicated amount of LPS was added. HEK/TLR4(+) response was measured by NFκB-activated luciferase expression determined six hours after addition of LPS. The anti-CXCR4 antibodies enhanced responsiveness of HEK/TLR4(+) cells to LPS.

To determine whether CXCR4 influences TLR4 activation by LPS, a model using HEK 293 cells, which naturally express CXCR4 (FIG. 6A) but not TLR4, was developed. The HEK 293 cells were made to express defined components of the TLR4 complex by transfection with vectors encoding murine TLR4, MD2, and CD14 and selection of clones that stably express these polypeptides (HEK/TLR4(+) cells). HEK 293 cells transfected this way respond to LPS and heparan sulfate (FIG. 6B).

To determine whether CXCR4 influences activation of TLR4 by LPS, HEK/TLR4(+) cells were transfected with NFκB-firefly-luciferase and internal control Renilla-luciferase reporter plasmids, and then the impact of inhibition of CXCR4 on TLR4 signaling was measured. When HEK/TLR4(+) cells were treated with anti-CXCR4 antibodies that perturb the conformation and function of the receptor, responses to low concentrations of LPS (less than 3 ng/mL) were increased nearly two fold compared to HEK/TLR4(+) cells treated with control IgG (FIG. 6C). Anti-CXCR4 antibodies did not modify activation of HEK/TLR4(+) by higher concentrations of LPS (10 ng/mL). This result demonstrates that CXCR4 can raise the threshold for TLR4 activation.

Figure 7:
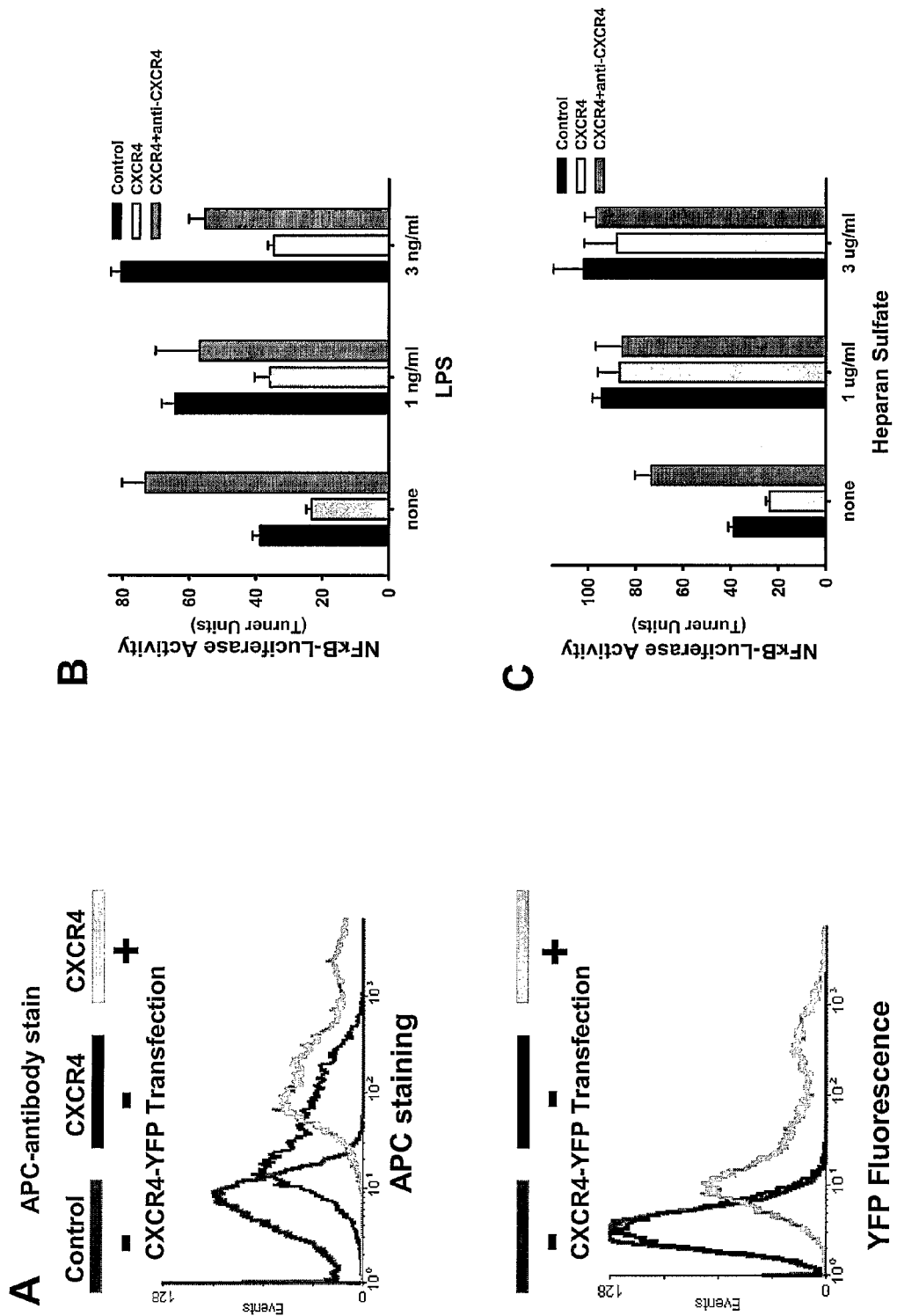
FIG. 7. Effect of enhanced expression of CXCR4 on TLR4 activation. To determine whether CXCR4 diminishes responsiveness to LPS, HEK/TLR4(+) cells were transfected with a vector encoding human CXCR4 fused to yellow fluorescent protein (CXCR4-YFP) or control expression plasmids, along with NFκB- and control-luciferase reporter plasmids and responsiveness to LPS was determined. (A) CXCR4 expression in HEK/TLR4(+) cells transfected with CXCR4-YFP. HEK/TLR4(+) cells were transfected with CXCR4-YFP vector, and CXCR4 expression on the surface of the cells was determined using an anti-CXCR4 monoclonal antibodies conjugated to APC (upper panel) or by directly measuring CXCR4-YFP fluorescence (lower panel). These results demonstrate that HEK/TLR4(+) cells transfected with CXCR4-YFP express CXCR4 at about 5 fold higher level than controls. (B) Enhanced expression of CXCR4 decreases responsiveness of HEK/TLR4(+) cells to LPS. HEK/TLR4(+) cells were transfected with CXCR4-YFP or control expression vectors along with NFκB and control-luciferase reporter plasmids, and responsiveness of the cells to LPS was determined. Some samples were treated with 25 μg/mL anti-CXCR4 monoclonal antibodies (anti-CXCR4) prior to stimulation with LPS. HEK/TLR4(+) cells transfected with CXCR4 did not respond to LPS. HEK/TLR4(+) cells transfected with CXCR4 and treated with anti-CXCR4 antibodies activated the NFκB-luciferase reporter fully. These results indicate that cell surface expression of CXCR4 interferes with TLR4 activation by LPS. (C) Control of TLR4 signaling by CXCR4 is observed with LPS and not the tested doses of heparan sulfate. To determine if suppression of TLR4 by CXCR4 is observed with heparan sulfate, HEK/TLR4(+) cells were transfected with CXCR4 or control expression plasmids and NFκB- and control-luciferase reporter plasmids, and responsiveness to heparan sulfate, an endogenous activator of TLR4, was tested. CXCR4 expression, or neutralization of CXCR4 function with anti-CXCR4 monoclonal antibodies, did not affect activation of HEK/TLR4(+) cells by heparan sulfate. This result indicates that CXCR4 interferes with activation of TLR4 by LPS, but not heparan sulfate at the doses tested.

To test this possibility that over-expression of CXCR4 might potentiate the inhibition, HEK/TLR4(+) cells were transfected with a plasmid vector encoding human CXCR4 and the NFκB- and control-luciferase reporter plasmids. Once transfected, the cells were tested for responses to LPS. The HEK/TLR4(+) cells transfected with CXCR4 expressed that polypeptide at five-fold greater levels than controls (FIG. 7A) and did not respond to LPS (FIG. 7B). To confirm that heightened expression of CXCR4 and not some other factor suppressed TLR4 signaling, HEK/TLR4(+) cells that had been transfected with CXCR4 were treated with anti-CXCR4 monoclonal antibodies and then stimulated with LPS. HEK/TLR4(+) cells transfected with CXCR4 and treated with anti-CXCR4 antibodies responded by activating the NFκB-luciferase reporter, confirming that CXCR4 had suppressed TLR4 signaling (FIG. 7B).

Figure 8:
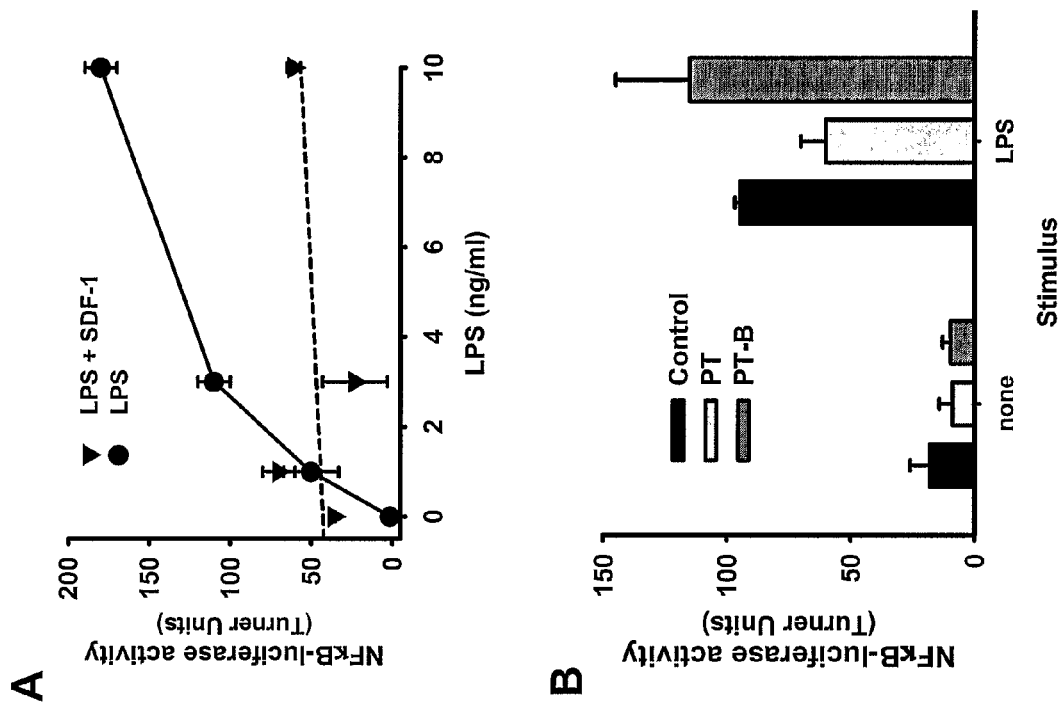
FIG. 8. Effect of signaling by CXCR4 on TLR4 activation. To determine if the inhibitory effect of CXCR4 on TLR4 activation requires signaling by CXCR4, HEK/TLR4(+) cells were transfected with NFκB- and control-luciferase reporter plasmids and treated with the CXCR4 agonist SDF-1, or with pertussis toxin (PT), an inhibitor of CXCR4 signaling, prior to stimulating the cells with LPS. (A) CXCR4 signaling inhibits TLR4 activation by LPS. To determine if CXCR4 signaling inhibits TLR4 activation by LPS, HEK/TLR4(+) cells were transfected with NFκB- and control-luciferase plasmids and treated with 50 nM SDF-1, an agonist of CXCR4, and stimulated with the indicated concentrations of LPS. Stimulation of CXCR4 by SDF-1 suppressed TLR4 activation by LPS. (B) Effect of Pertussis toxin on activation of TLR4 by LPS. To determine which signals from CXCR4 inhibit activation of TLR4 by LPS, HEK/TLR4(+) cells were transfected with NFκB- and control luciferase plasmids and treated with 0.1 μg/mL pertussis toxin (PT), which inhibits CXCR4 signaling by modifying receptor-associated $G_i$. Controls included HEK/TLR4(+) cells treated with the pertussis toxin B oligomer (PT-B), which binds to cells but does not inhibit CXCR4 signaling. Pertussis toxin did not enhance but instead inhibited LPS-stimulated HEK/TLR4(+) activation. These results indicate that signaling by CXCR4 inhibits activation of TLR4 by LPS, and this effect is likely mediated by the βγ component of CXCR4.

To determine if CXCR4 must be activated to suppress stimulation of TLR4 by LPS, the ability of increasing availability of SDF-1, the agonist for CXCR4 (Proudfoot, *Nat. Rev. Immunol.*, 2:106-115 (2002)), to potentiate inhibition of HEK/TLR4(+) cell responses to LPS was tested. When HEK/TLR4(+) cells were stimulated simultaneously with LPS and SDF-1, the cells were indifferent to the presence of LPS at any concentration tested (FIG. 8A). SDF-1 by itself initiated a slight activation of the luciferase reporter, consistent with findings that CXCR4 is a weak stimulator of NFκB (Ye, *J. Leukoc. Biol.*, 70:839-848 (2001)), but this level of activation is far below that observed for LPS treatment alone. Treatment of HEK/TLR4 cells with SDF-1 did not alter expression of TLR4, demonstrating that signals delivered through CXCR4 strongly inhibit activation of TLR4 signaling by LPS.

To determine whether an inhibition of TLR4 by CXCR4 is observed with an endogenous activator of TLR4, HEK/TLR4(+) cells transfected with CXCR4 and NFκB- and control-luciferase reporter plasmids were tested for response to heparan sulfate. HEK/TLR4(+) cells responded fully to heparan sulfate despite overexpression of CXCR4, and treatment of HEK/TLR4(+) cells with anti-CXCR4 antibodies did not influence responsiveness to heparan sulfate (FIG. 7C). These results indicate that CXCR4 constrains signaling by TLR4 induced by LPS and not heparan sulfate at the doses tested. Failure of CXCR4 to inhibit activation of TLR4 by heparan sulfate has several potential explanations. Heparan sulfate may act somewhat differently on TLR4 than does LPS. Alternatively, the added soluble heparan sulfate might elute SDF-1 from its cellular attachments, primarily heparan sulfate proteoglycans on the cell surface (Netelenbos et al., *Leukemia*, 17:175-184 (2003)), and prevent the SDF-1-stimulated TLR4-inhibitor function.

Since signaling by CXCR4 suppresses activation of TLR4 by LPS, interference with CXCR4 signaling should enhance HEK/TLR4(+) activation by LPS. To test this possibility, HEK/TLR4(+) cells were treated with pertussis toxin, a polypeptide that inhibits signaling of G proteins such as $G_i$ associated with CXCR4 (Sotsios et al., *J. Immunol.*, 163:5954-5963 (1999)), and tested responses of the cells to LPS. Pertussis toxin did not enhance HEK/TLR4 activation by LPS, rather treatment of HEK/TLR4(+) cells with pertussis toxin diminished TLR4 activation by LPS (FIG. 8B). Since inhibition of CXCR4-associated $G_i$ by pertussis toxin did not increase activation of TLR4 by LPS, the inhibitory signal delivered by CXCR4 is likely mediated by the βγ subunit of this heterotrimeric G-protein coupled receptor.

The results provided herein indicate that interaction of SDF-1 and CXCR4 with TLR4 raises the threshold for activation of inflammatory cells by TLR4. This change in threshold does not prevent activation of TLR4 by "large" amounts of LPS, but it may prevent inadvertent activation by trace amounts, as may occur at tissue sites remote from the site of infection. These results may explain why local infections with Gram negative bacteria usually do not cause the systemic manifestations of sepsis. Since the CXCR4 expression did not change the threshold for activation of TLR4 by heparan sulfate, other local controls may exist for this agonist.

The results provided herein also demonstrate that antibodies capable of blocking CXCR4 function can enhance TLR4 signaling, while increased expression of CXCR4 or addition of the CXCR4 ligand SDF-1 can suppress TLR4 signaling induced by LPS.

CXCR4 may coordinate a balance between promoting and inhibiting inflammation. SDF-1 acting on CXCR4 directs migration CD3+ lymphocytes into areas of inflammation, and recent evidence demonstrates that this pro-inflammatory property of SDF-1 is silenced by proteases secreted by activated neutrophils (Rao et al., *J. Exp. Med.*, 200:713-724 (2004)). The results provided herein demonstrate that SDF-1 and CXCR4 may also limit inappropriate inflammatory cues by raising the activation threshold for TLR4. The interplay between the pro- and anti-inflammatory properties of SDF-1, CXCR4, and TLR4 offer new targets to potentially manipulate immune function.

Example 3

Reducing Expression of CXCR4 Enhances TLR4 Responsiveness

HEK 293 cells stabily expressing TLR4, MD2, and CD14 (HEK/TLR4(+) cells) were transfected with a CXCR4 RNAi-expressing vector designed to reduce the expression of CXCR4 polypeptides. The vector contained a DNA sequence that, when transcribed by the cell, encodes an RNA molecule that is complementary to a region of naturally occurring cellular CXCR4 mRNA. Interaction of this small, interfering RNA, or "siRNA" molecule with cellular CXCR4 mRNA results in degradation of the cellular CXCR4 mRNA and thus reduces expression of the cellular CXCR4 polypeptide molecule. The CXCR4 RNAi-expressing vector targeted a region of human CXCR4 beginning with nucleotide 286 of the coding sequence and included the following nucleic acid sequence: GAT CCC CGA AGA AAC TGA GAA GCA TGT TCA AGA GAC ATG CTT CTC AGT TTC TTC TTT TTG GAA A (SEQ ID NO:21) followed by an intervening loop step loop structure followed by AGC TTT TCC AAA AAG AAG AAA CTG AGA AGC ATG TCT CTT GAA CAT GCT TCT CAG TTT CTT CGG G (SEQ ID NO:22).

Figure 9:
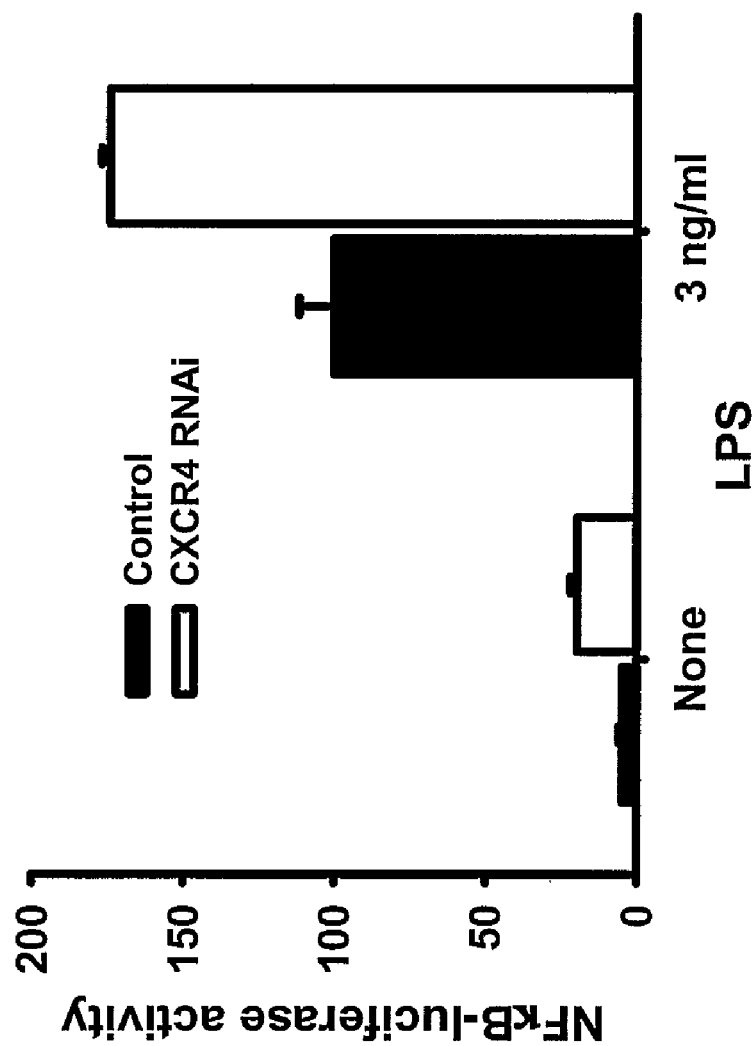
FIG. 9 is a bar graph plotting NFκB-luciferase activity for LPS-treated and untreated cells transfected with and without a CXCR4 RNAi-expressing vector.

After transfection, the cells were treated with LPS, and the level of TLR4 activity was measured. Cells transfected with the CXCR4 RNAi-expression vector exhibited enhanced responsiveness to LPS (FIG. 9). These results indicate that unperturbed CXCR4 interferes with TLR4 activation.

Example 4

Production and Purification of a Polypeptide Having SDF-1 Activity

To produce a recombinant, histidine-tagged murine SDF-1 polypeptide in *E. coli*, a cDNA encoding a mouse SDF-1 polypeptide was cloned into a bacterial expression vector 3' to an in-frame sequence encoding six histidine residues. The vector encoding the [Hisx6]SDF-1 polypeptide was transformed into *E. coli*, and recombinant protein production was induced using IPTG. Uninduced (control) or induced *E. coli* were lysed, and cellular polypeptides were separated by molecular size using SDS-PAGE. The total cellular extracts as well as soluble or insoluble fractions were evaluated for the recombinant [Hisx6]SDF-1 polypeptide by staining the gels with Coomassie blue. The [Hisx6]SDF-1 polypeptide was highly induced in *E. coli* and was contained completely in the insoluble component of cell extracts.

To determine if recombinant SDF-1 polypeptides react with SDF-1 polypeptide-specific antibodies, *E. coli* were transformed with expression vectors encoding a murine SDF-1 polypeptide fused to glutathione S-transferase (GST) or hexahistidine tags and were induced with IPTG. Cell extracts were prepared and the polypeptides resolved according to molecular size by SDS-PAGE and transferred to PVDF membranes. The membranes were probed, and the SDF-1 polypeptides revealed by immunoblot using polyclonal antibodies against mouse SDF-1. A completely synthetic SDF-1 polypeptide was used as a control. The immunoblot revealed that a bacterially-produced recombinant SDF-1 polypeptide is reactive with anti-SDF-1 polypeptide antibodies.

To produce a purified, recombinant murine [Hisx6]SDF-1 polypeptide preparation, expression of a [Hisx6]SDF-1 polypeptide was induced in *E. coli*. The [Hisx6]SDF-1 polypeptide was solubilized with 6M Urea and purified by nickel-agarose affinity chromatography. Fractions containing the [Hisx6]SDF-1 polypeptide were pooled, and different amounts of polypeptide were subjected to SDS-PAGE and Coomassie blue staining. The results revealed a highly purified (>90%) [Hisx6]SDF-1 polypeptide preparation.

To determine if the purified, recombinant [Hisx6]SDF-1 polypeptide activates CXCR4, Jurkat T cells were stimulated (37° C. for 30 minutes) with buffer alone or with buffer containing a synthetic SDF-1 polypeptide or the purified recombinant [Hisx6]SDF-1 polypeptide. Control cells were stimulated with bovine albumin. The treated cells were stained with fluorochrome-labeled anti-CXCR4 antibodies, and the amount of CXCR4 on the cell surface was measured by the intensity of CXCR4 antibody staining using FACS. The results revealed that recombinant [Hisx6]SDF-1 polypeptides stimulate a decrease in CXCR4 on cell surfaces, reflecting SDF-1 polypeptide-stimulated internalization of CXCR4.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for decreasing Toll-like receptor-4 activation in cells, wherein said cells are in the presence of a Toll-like receptor-4 agonist selected from LPS and heparin sulfate, and wherein said cells are in a mammal with inflammation symptoms as a result of an inflammatory condition, said method comprising:
    administering an SDF-1 polypeptide to said cells under conditions wherein the level of said Toll-like receptor-4 activation in said cells is decreased thereby reducing the level of inflammation symptoms in said mammal, and determining the severity of said symptoms after said administering.

2. The method of claim 1, wherein said cells are leukocytes, endothelial cells, or parenchymal cells.

3. The method of claim 1, wherein said Toll-like receptor-4 agonist is LPS.

4. The method of claim 1, wherein said mammal is a human.

* * * * *

SEQUENCE LISTING

<160> NUMBER OF SEQ ID NOS: 22

<210> SEQ ID NO 1
<211> LENGTH: 1940

```
<212> TYPE: DNA
<213> ORGANISM: Homo sapiens

<400> SEQUENCE: 1
gccgcacttt cactctccgt cagccgcatt gcccgctcgg cgtccggccc ccgacccgcg      60
ctcgtccgcc cgcccgcccg cccgcccgcg ccatgaacgc caaggtcgtg gtcgtgctgg     120
tcctcgtgct gaccgcgctc tgcctcagcg acgggaagcc cgtcagcctg agctacagat     180
gcccatgccg attcttcgaa agccatgttg ccagagccaa cgtcaagcat ctcaaaattc     240
tcaacactcc aaactgtgcc cttcagattg tagcccggct gaagaacaac aacagacaag     300
tgtgcattga cccgaagcta agtggattca ggagtacct ggagaaagct ttaaacaagt      360
aagcacaaca gccaaaaagg actttccgct agacccactc gaggaaaact aaaaccttgt     420
gagagatgaa agggcaaaga cgtggggggag ggggccttaa ccatgaggac caggtgtgtg    480
tgtggggtgg gcacattgat ctgggatcgg gcctgaggtt tgccagcatt tagaccctgc     540
atttatagca tacggtatga tattgcagct tatattcatc catgccctgt acctgtgcac     600
gttggaactt ttattactgg ggttttttcta agaaagaaat tgtattatca acagcatttt   660
caagcagtta gttccttcat gatcatcaca atcatcatca ttctcattct cattttttaa    720
atcaacgagt acttcaagat ctgaatttgg cttgtttgga gcatctcctc tgctcccctg    780
gggagtctgg gcacagtcag gtggtggctt aacagggagc tggaaaaagt gtcctttctt    840
cagacactga ggctcccgca gcagcgcccc tcccaagagg aaggcctctg tggcactcag    900
ataccgactg gggctgggcg ccgccactgc cttcacctcc tctttcaacc tcagtgattg    960
gctctgtggg ctccatgtag aagccactat tactgggact gtgctcagag accctctcc   1020
cagctattcc tactctctcc ccgactccga gagcatgctt aatcttgctt ctgcttctca   1080
tttctgtagc ctgatcagcg ccgcaccagc cgggaagagg gtgattgctg ggctcgtgc   1140
cctgcatccc tctcctccca gggcctgccc cacagctcgg gccctctgtg agatccgtct   1200
ttggcctcct ccagaatgga gctggccctc tcctggggat gtgtaatggt ccccctgctt   1260
acccgcaaaa gacaagtctt tacagaatca aatgcaattt taaatctgag agctcgcttt   1320
gagtgactgg gttttgtgat tgcctctgaa gcctatgtat gccatggagg cactaacaaa   1380
ctctgaggtt tccgaaatca gaagcgaaaa aatcagtgaa taaaccatca tcttgccact   1440
acccctcct gaagccacag cagggtttca ggttccaatc agaactgttg gcaaggtgac    1500
atttccatgc ataaatgcga tccacagaag gtcctggtgg tatttgtaac ttttttgcaag  1560
gcatttttt atatatattt ttgtgcacat ttttttttac gtttctttag aaaacaaatg    1620
tatttcaaaa tatatttata gtcgaacaat tcatatattt gaagtggagc catatgaatg   1680
tcagtagttt atacttctct attatctcaa actactggca atttgtaaag aaatatatat   1740
gatatataaa tgtgattgca gcttttcaat gttagccaca gtgtattttt tcacttgtac   1800
taaaattgta tcaaatgtga cattatatgc actagcaata aatgctaat tgtttcatgg    1860
tataaacgtc ctactgtatg tgggaattta tttacctgaa ataaaattca ttagttgtta   1920
gtgatggagc ttaaaaaaaa                                               1940

<210> SEQ ID NO 2
<211> LENGTH: 1837
<212> TYPE: DNA
<213> ORGANISM: Mus musculus

<400> SEQUENCE: 2
gaccactttc actctcggtc cacctcggtg tcctcttgct gtccagctct gcagcctccg      60
```

```
gcgcgccctc cgcccacgc catggacgcc aaggtcgtcg ccgtgctggc cctggtgctg      120
gccgcgctct gcatcagtga cggtaaacca gtcagcctga gctaccgatg cccctgccgg      180
ttcttcgaga gccacatcgc cagagccaac gtcaagcatc tgaaaatcct caacactcca      240
aactgtgccc ttcagattgt tgcacggctg aagaacaaca acagacaagt gtgcattgac      300
ccgaaattaa agtggatcca agagtacctg gagaaagctt taaacaagta agcacaacag      360
cccaaaggac tttccagtag accccgagg aaggctgaca tccgtgggag atgcaagggc       420
agtggtgggg aggagggcct gaaccctggc caggatggcc ggcgggacag cactgactgg      480
ggtcatgcta aggtttgcca gcataaagac actccgccat agcatatggt acgatattgc      540
agcttatatt catccctgcc ctcgcccgtg cacaatggag cttttataac tggggttttt      600
ctaaggaatt gtattaccct aaccagttag cttcatcccc attctcctca tcctcatctt      660
cattttaaaa agcagtgatt acttcaaggg ctgtattcag tttgctttgg agcttctctt      720
tgccctgggg cctctgggca cagttataga cggtggcttt gcagggagcc ctagagagaa      780
accttccacc agagcagagt ccgaggaacg ctgcagggct tgtcctgcag ggggcgctcc      840
tcgacagatg ccttgtcctg agtcaacaca agatccggca gagggaggct cctttatcca      900
gttcagtgcc agggtcggga agcttccttt agaagtgatc cctgaagctg tgctcagaga      960
ccctttccta gccgttcctg ctctctgctt gcctccaaac gcatgcttca tctgacttcc     1020
gcttctcacc tctgtagcct gacggaccaa tgctgcaatg aagggagga gagtgatgtg      1080 gggtgccccc tccctctctt ccctttgctt tcctctcact tgggccctt gtgagatttt       1140 tctttggcct cctgtagaat ggagccagac catcctggat aatgtgagaa catgcctaga      1200
tttacccaca aaacacaagt ctgagaatta atcataaacg gaagtttaaa tgaggatttg      1260
gactttggta attgtccctg agtcctatat atttcaacag tggctctatg ggctctgatc      1320
gaatatcagt gatgaaaata ataataataa taataataac gaataagcca gaatcttgcc      1380
atgaagccac agtggggatt ctgggttcca atcagaaatg gagacaagat aaaacttgca      1440
tacattctta tgatcacaga cggccctggt ggttttttggt aactatttac aaggcatttt      1500
tttacatata tttttgtgca ctttttatgt ttctttggaa gacaaatgta tttcagaata      1560
tatttgtagt caattcatat atttgaagtg gagccatagt aatgccagta gatatctcta      1620
tgatcttgag ctactggcaa cttgtaaaga aatatatatg acatataaat gtattgtagc      1680
tttccggtgt cagccacggt gtattttttcc acttggaatg aaattgtatc aactgtgaca      1740
ttatatgcac tagcaataaa atgctaattg tttcatgctg taaacctcct accgtatgtg      1800
ggaatttatt tacctgaaat aaaatctact agttgtt                               1837
```

<210> SEQ ID NO 3  
<211> LENGTH: 3132  
<212> TYPE: DNA  
<213> ORGANISM: Mus musculus

<400> SEQUENCE: 3

```
gaccactttc actctcggtc cacctcggtg tcctcttgct gtccagctct gcagcctccg       60
gcgcgccctc ccgcccacgc catggacgcc aaggtcgtcg ccgtgctggc cctggtgctg      120
gccgcgctct gcatcagtga cggtaaacca gtcagcctga gctaccgatg cccctgccgg      180
ttcttcgaga gccacatcgc cagagccaac gtcaagcatc tgaaaatcct caacactcca      240
aactgtgccc ttcagattgt tgcacggctg aagaacaaca acagacaagt gtgcattgac      300
ccgaaattaa agtggatcca agagtacctg gagaaagctt taaacaagag gctcaagatg      360
```

```
tgagaggtgt gagtcagacg cccgaggaac ttacaggagg agcctaggtc tgaagtcagt    420
gttagggaag ggcccatagc cacttcctct gctcctgagc agggctgaag ccgtttgcaa    480
gggacttgct ttgcacagtt ttgctgtact ttcacatttt attatgtagc aagatacatg    540 gtgattttt tttttttca tttagcctga ttttccaacg tcattggtga caggccaagg      600
ccactatgtt atttcctttg ttctggtatc cttcccttgg aggaccttct ctgagtagtg    660
gctccccagg tttgtccttt gagctgaggc aggaggctca cccattcttc tgaataggaa    720
ctgggtgttc ccaccccca aggactgcag ggctttccca agctgaggca ggaacgtgag     780
gccagggaag agtgagcttc accctcatcc cacgctgtcc tcctcaaccc accatgctca    840
tcattctgtc tcatccatcc atccatccat ccattcatcg ccatgtgtcc gcaagactgt    900
ctccatgacc ctgaaaaagg actctcgaga tgaaatcctt tattcaaatg ggacagcaag    960
aaggaaaagc caatgtctgg tgtctctccc cccgccccta ccctgcgcgc atctatgtct   1020
tgtttggaat attgtctctt caaccccctg ttcatgtcct tctcactcat gatcgatgtc   1080
ttgtctgtgc actgtctcta acccaaatgc aaaggctgag tgtgaggtga tggccccgag   1140
gtccaggttg tagtcatgga aagagccctg ctgtctccct tctcaggggg cccattttag   1200
acacacaaag cccaaagaaa ggtggtttgc aacagtgctt agctcgagcc tccatatttc   1260
cataactgtt agcttaaaac tgtggggttt taccttcctg gaaccaaatg cattcttctg   1320
ttgaggagta acaggtctca attctttca attaattta aaagtcaatc actaagagca     1380
tcggctttgg gccctgatgg gcaggcattt ccctggaaag ggggtgaact acctacctct   1440
cctcaagaca gccgaagggt gggattggtg ccgctctggg aagcgtggcc ccaggagttt   1500
tgtcctctgc agttttaat gcaagttcac tgccactttg acaaaagccc aattagaagc    1560
cagtctctag ttccttaaac aaaacagaca gagtaaggaa aggaaggagg gtggcagcca   1620
gctggctgga cactcgagaa agacgggaa gtaagctaca gaaagatagt cttcaaaaac    1680
aggtgtttga gagtgaatac tctgtagaat tgttagtggg gtgtgtgtgg tggtggtggg   1740
gggatttcta caaatagtc ctttaagttg agtttacagc agatgaaaaa tccaaccagc    1800
aaaattttga tcaaatttga acaaaaaccc aaaaacctaa aactgttgag caggttgcga   1860
tgaggagcac agggctagct gcagagctgg atcctcagga ggatagcgaa ttattttcaa   1920
ccctggaata gaaaccacac actggcttgc tgtgcaccag ccactttgca tctaatccaa   1980
gctttgaagg gtgttgcttg ggaggaaaca aatacagcct tccatcttca ctccagttag   2040
ggatcctttc aaagtctcct tcacagtgag gaaaagaga agggtagaaa ctttagggag    2100
ccggatttgt gtatcaattc ctccgctgac agtcagtttc tagatggaga cagcctgctt   2160
aaagcaaatc cgaatttaaa taggacattt acatcggaaa agtctctccc taccttaatc   2220
ccccattctc ttgctttcaa aatacaagca cagcagtcct tgaatggctg ttgacccagg   2280
gcacctagct gtccctgctg gtcctggggc tgccagaatt cccttgggcg ccaagcaacc   2340
tgccaggtag ccagtccctc tgttacaagc ctttgcatct ggatagggaa aggggtggag   2400
acatacagtc tgctttgtgt tgaaacccag atttgtaccc tgtgtttata cactgctgct   2460
ggctcccgag gacagtggga ctttagcaag gaagtgcagc cgaggggtaa agagccctct   2520
ggttcattgc ctgatcggct ttgagagagg gtttggaggg caaggggctg cattcctctg   2580
agggacttgg cctgaggcct ttcgggcctc tccagtgggt tctgtttatc ctctcatggg   2640
tgattatctc agtggtgtca ccaggggctt cctcccagaa gtcagtcatc cccaggccgt   2700
gcaccctttt cagctggatg agagccaggg atgcattctc tccaaacagc taccctggcc   2760
```

```
cattttaagg taatctcatt cttcaaaatg ttccatagaa tcctccaaat tcccccagca   2820
gacttctacc ctcgccaagt tcccaaaacc cactcagcaa agttgccaac ctcgacgggc   2880
tagcagtgtc taagcagcga tgggttcagt gttgtgtgtg gtgaatactg tattttgttt   2940
cagttctgtc tcccagataa tgtgaaaacg gtccaggaga aggcagcttc ctatatgcag   3000
cgtgtgcttt cttattctta tttttaatat atgacagtta tttgagaagc catttctact   3060
ttgaagtcat tatcgatgaa agtgatgtat cttcacctac cattttccta ataaagttct   3120
gtattcaaat at                                                      3132
```

<210> SEQ ID NO 4
<211> LENGTH: 88
<212> TYPE: PRT
<213> ORGANISM: Homo sapiens

<400> SEQUENCE: 4

```
Met Asn Ala Lys Val Val Val Leu Val Leu Val Leu Thr Ala Leu
 1               5                   10                  15

Cys Leu Ser Asp Gly Lys Pro Val Ser Leu Ser Tyr Arg Cys Pro Cys
                20                  25                  30

Arg Phe Phe Glu Ser His Val Ala Arg Ala Asn Val Lys His Leu Lys
            35                  40                  45

Ile Leu Asn Thr Pro Asn Cys Ala Leu Gln Ile Val Ala Arg Leu Lys
        50                  55                  60

Asn Asn Asn Arg Gln Val Cys Ile Asp Pro Lys Leu Lys Trp Ile Gln
65                  70                  75                  80

Glu Tyr Leu Glu Lys Ala Leu Asn
                85
```

<210> SEQ ID NO 5
<211> LENGTH: 89
<212> TYPE: PRT
<213> ORGANISM: Mus musculus

<400> SEQUENCE: 5

```
Met Asp Ala Lys Val Val Ala Val Leu Ala Leu Val Leu Ala Ala Leu
 1               5                   10                  15

Cys Ile Ser Asp Gly Lys Pro Val Ser Leu Ser Tyr Arg Cys Pro Cys
                20                  25                  30

Arg Phe Phe Glu Ser His Ile Ala Arg Ala Asn Val Lys His Leu Lys
            35                  40                  45

Ile Leu Asn Thr Pro Asn Cys Ala Leu Gln Ile Val Ala Arg Leu Lys
        50                  55                  60

Asn Asn Asn Arg Gln Val Cys Ile Asp Pro Lys Leu Lys Trp Ile Gln
65                  70                  75                  80

Glu Tyr Leu Glu Lys Ala Leu Asn Lys
                85
```

<210> SEQ ID NO 6
<211> LENGTH: 93
<212> TYPE: PRT
<213> ORGANISM: Mus musculus

<400> SEQUENCE: 6

```
Met Asp Ala Lys Val Val Ala Val Leu Ala Leu Val Leu Ala Ala Leu
 1               5                   10                  15

Cys Ile Ser Asp Gly Lys Pro Val Ser Leu Ser Tyr Arg Cys Pro Cys
                20                  25                  30
```

```
Arg Phe Phe Glu Ser His Ile Ala Arg Ala Asn Val Lys His Leu Lys
         35                  40                  45

Ile Leu Asn Thr Pro Asn Cys Ala Leu Gln Ile Val Ala Arg Leu Lys
 50                  55                  60

Asn Asn Asn Arg Gln Val Cys Ile Asp Pro Lys Leu Lys Trp Ile Gln
 65                  70                  75                  80

Glu Tyr Leu Glu Lys Ala Leu Asn Lys Arg Leu Lys Met
                 85                  90

<210> SEQ ID NO 7
<211> LENGTH: 8
<212> TYPE: PRT
<213> ORGANISM: Artificial Sequence
<220> FEATURE:
<223> OTHER INFORMATION: domain from SDF-1 polypeptide that interacts
      with CXCR4 polypeptide

<400> SEQUENCE: 7

Lys Pro Leu Ser Leu Ser Tyr Arg
 1               5

<210> SEQ ID NO 8
<211> LENGTH: 8
<212> TYPE: PRT
<213> ORGANISM: Artificial Sequence
<220> FEATURE:
<223> OTHER INFORMATION: domain from SDF-1 polypeptide that interacts
      with CXCR4 polypeptide

<400> SEQUENCE: 8

Lys Pro Ile Ser Leu Ser Tyr Arg
 1               5

<210> SEQ ID NO 9
<211> LENGTH: 8
<212> TYPE: PRT
<213> ORGANISM: Artificial Sequence
<220> FEATURE:
<223> OTHER INFORMATION: domain from SDF-1 polypeptide that interacts
      with CXCR4 polypeptide

<400> SEQUENCE: 9

Lys Leu Val Ser Leu Ser Tyr Arg
 1               5

<210> SEQ ID NO 10
<211> LENGTH: 8
<212> TYPE: PRT
<213> ORGANISM: Artificial Sequence
<220> FEATURE:
<223> OTHER INFORMATION: domain from SDF-1 polypeptide that interacts
      with CXCR4 polypeptide

<400> SEQUENCE: 10

Lys Ile Val Ser Leu Ser Tyr Arg
 1               5

<210> SEQ ID NO 11
<211> LENGTH: 8
<212> TYPE: PRT
<213> ORGANISM: Artificial Sequence
<220> FEATURE:
<223> OTHER INFORMATION: domain from SDF-1 polypeptide that interacts
      with CXCR4 polypeptide

<400> SEQUENCE: 11
```

```
Lys Leu Ile Ser Leu Ser Tyr Arg
1               5

<210> SEQ ID NO 12
<211> LENGTH: 8
<212> TYPE: PRT
<213> ORGANISM: Artificial Sequence
<220> FEATURE:
<223> OTHER INFORMATION: domain from SDF-1 polypeptide that interacts
      with CXCR4 polypeptide

<400> SEQUENCE: 12

Lys Ile Leu Ser Leu Ser Tyr Arg
1               5

<210> SEQ ID NO 13
<211> LENGTH: 8
<212> TYPE: PRT
<213> ORGANISM: Artificial Sequence
<220> FEATURE:
<223> OTHER INFORMATION: domain from SDF-1 polypeptide that interacts
      with CXCR4 polypeptide

<400> SEQUENCE: 13

Arg Lys Arg Arg Ala Ala Arg Arg
1               5

<210> SEQ ID NO 14
<211> LENGTH: 8
<212> TYPE: PRT
<213> ORGANISM: Artificial Sequence
<220> FEATURE:
<223> OTHER INFORMATION: domain from SDF-1 polypeptide that interacts
      with CXCR4 polypeptide

<400> SEQUENCE: 14

Lys Pro Val Ser Leu Ser Tyr Arg
1               5

<210> SEQ ID NO 15
<211> LENGTH: 30
<212> TYPE: DNA
<213> ORGANISM: Artificial Sequence
<220> FEATURE:
<223> OTHER INFORMATION: oligonucleotide

<400> SEQUENCE: 15
cgcggatcca ggatgatgcc tccctggctc                                    30

<210> SEQ ID NO 16
<211> LENGTH: 30
<212> TYPE: DNA
<213> ORGANISM: Artificial Sequence
<220> FEATURE:
<223> OTHER INFORMATION: oligonucleotide

<400> SEQUENCE: 16
ggcggtacct caggtccaag ttgccgtttc                                    30

<210> SEQ ID NO 17
<211> LENGTH: 20
<212> TYPE: DNA
<213> ORGANISM: Artificial Sequence
<220> FEATURE:
<223> OTHER INFORMATION: oligonucleotide

<400> SEQUENCE: 17
ccggaattca tcatgttgcc                                               20
```

```
<210> SEQ ID NO 18
<211> LENGTH: 24
<212> TYPE: DNA
<213> ORGANISM: Artificial Sequence
<220> FEATURE:
<223> OTHER INFORMATION: oligonucleotide

<400> SEQUENCE: 18
ccggaattcc taattgacat cacg                                          24

<210> SEQ ID NO 19
<211> LENGTH: 30
<212> TYPE: DNA
<213> ORGANISM: Artificial Sequence
<220> FEATURE:
<223> OTHER INFORMATION: oligonucleotide

<400> SEQUENCE: 19
ccggaattca ccatggagcg tgtgcttggc                                    30

<210> SEQ ID NO 20
<211> LENGTH: 33
<212> TYPE: DNA
<213> ORGANISM: Artificial Sequence
<220> FEATURE:
<223> OTHER INFORMATION: oligonucleotide

<400> SEQUENCE: 20
ccggaattct taaacaaaga ggcgatctcc tag                                33

<210> SEQ ID NO 21
<211> LENGTH: 64
<212> TYPE: DNA
<213> ORGANISM: Artificial Sequence
<220> FEATURE:
<223> OTHER INFORMATION: oligonucleotide

<400> SEQUENCE: 21
gatccccgaa gaaactgaga agcatgttca agagacatgc ttctcagttt cttcttttg    60 gaaa                                                                64

<210> SEQ ID NO 22
<211> LENGTH: 64
<212> TYPE: DNA
<213> ORGANISM: Artificial Sequence
<220> FEATURE:
<223> OTHER INFORMATION: oligonucleotide

<400> SEQUENCE: 22
agcttttcca aaaagaagaa actgagaagc atgtctcttg aacatgcttc tcagtttctt   60
cggg                                                                64
```